US007094760B2

(12) United States Patent
Mathison et al.

(10) Patent No.: US 7,094,760 B2
(45) Date of Patent: Aug. 22, 2006

(54) PEPTIDES FOR TREATMENT OF INFLAMMATION AND SHOCK

(75) Inventors: Ronald Mathison, Calgary (CA); Joseph S. Davison, Calgary (CA); Dean Befus, Edmonton (CA); Graham Moore, Calgary (CA)

(73) Assignee: Salpep Biotechnology, Inc., Calgary (CA)

( * ) Notice: Subject to any disclaimer, the term of this patent is extended or adjusted under 35 U.S.C. 154(b) by 0 days.

(21) Appl. No.: 10/773,229

(22) Filed: Feb. 9, 2004

(65) Prior Publication Data

US 2004/0142874 A1 Jul. 22, 2004

Related U.S. Application Data

(62) Division of application No. 09/051,395, filed as application No. PCT/CA97/00568 on Aug. 13, 1997, now Pat. No. 6,852,697.

(30) Foreign Application Priority Data

Aug. 13, 1996 (GB) ................................ 9617021.2

(51) Int. Cl.
 *A61K 38/08* (2006.01)
(52) U.S. Cl. ............................ 514/16; 514/17; 514/18; 530/328; 530/329; 530/330; 530/331
(58) Field of Classification Search .................... 514/2, 514/16, 17, 18; 530/324, 328, 330, 331
See application file for complete search history.

(56) References Cited

U.S. PATENT DOCUMENTS 4,880,779 A 11/1989 Gallaher
6,586,403 B1 * 7/2003 Mathison et al. ............. 514/18

FOREIGN PATENT DOCUMENTS

WO WO 92/11858 7/1992

OTHER PUBLICATIONS

Ngo et al. Computational Complexity, Protein Structure Prediction, and the Levinthal Paradox. The protein folding problem and Tertiary Structure Prediction. Ed. K. merz and L. Le Grand. Birkhauser, Boston, Ma. pp. 491-495. 1994.*
Rudinger, J. (1976). Peptide Hormones (Ed. J. A. Parsons). University Park Press. Baltimore. pp. 1-7.*
The Merck Manual of Diagnosis and Therapy. 16th ed. Ed. Robert Berkow. Rathway, NJ: Merck Research Laboratories, 1992. 830-839, 1305-1312.*
Mathison et al., "Neural regulation of neutrophil involvement in pulmonary inflammation," *Comp. Physiol.*, 1993, pp. 39-48, vol. 106C, No. 1, Springer-Verlag Heidelberg, Heidelberg, Germany.
Bachem Feinchemikalien AG, Hauptstrasse 144, CH-4416 Bubendorf/Switzerland, *Bachem Catalog S13*, 1993, pp. 203 and 522, Abstract No. XP002051006.

Abderhalden et al., "Ubr das Verhalten von Tetrapeptiden gegenüber Erepsin und Trypsin, an deren Aufbau Glykokoll (2 Mol), 1(+)-Alanin (1 Mol) und 1(-)-Tyrosin (1 Mol) beteiligt sind", *Fermentforschung*, 1942, pp. 98-114, vol. 16.
Slootstra, "Structural aspects of antibody-antigen interaction revealed through small random peptide libraries", *Molecular Diversity*, 1996, pp. 87-96, vol. 1, Kluwer Academic Publishers, Basel, Switzerland.
Mathison et al., "Submandibular glands: novel structures . . . ", *Can J. of Physiol. Pharmacol.*, 1997, pp. 407-413, vol. 75, Abstract No. XP992051009, National Research Council of Canada, Ottaw, Ontario, Canada.
Grant, "Synthetic Peptides: A User's Guide," Freeman & Company, 1992, p. 53.
Wilkes et al., "Critical Ionizing Groups in Aeromonas Neutral Protease," *J. Biol. Chem.*, 1988, pp. 1821-1825, vol. 263, No. 4, Walter de Gruyter, Berlin, Germany.
Mathison et al., "Temporal analysis of the anti-inflammatory effects of decentralization of the superior cervical ganglia," *American Journal of Physiol.*, 1994, pp. R1537-R1543, vol. 266, American Physiological Society, Bethesda, MD.
Mathison et al., Removal of the submandibular glands increases the acute hypotensive response to endotoxin, *Circulatory Shock*, 1993, pp. 52-58, vol. 39, Wiley-Liss, Inc., New York, New York.
Ngo et al., Computational Complexity, Potein Structure Prediction, and the Levinthal Paradox, The Protein Folding Problem and Tertiary Structure Prediction, 1994, Ed. K. Merz and L. Le Grand, BirkHauser, Boston, MA, pp. 491-495.
Rudinger, "Characteristics of the amino acids as components of a peptide hormone sequence," *Peptide Hormones*, Ed. J.A. Parsons, National Institute for Medical Research, Mill Hill, London, University Park Press, Baltimore, MD, pp. 1-7, 1976.
Barka, "Biologically Active Polypeptides in Submandibular Glands," *The Journal of Histochemistry and Cytochemistry*, 1980, pp. 836-859, vol. 28, No. 8, The Histochemical Society/High Wire Press, New York, New York.
Boyer et al., "Une fonction non exocrine de la glande sous-maxillaire," *Annales d'Endocrinologie*, 1991, pp. 307-322, vol. 52, Paris, France.
Mathison et al., "Neuroendocrine regulation of inflammation and tissue repair by submandibular gland factors," *Immunology Today*, 1994, pp. 527-531, vol. 15, No. 11, Elsevier Science, Ltd., England.
Epstein et al., "The role of saliva in oral health and the causes and effects of xerostomia," *The Canadian Dental Association Journal*, 1992, pp. 217-221, vol. 58.

(Continued)

*Primary Examiner*—Anish Gupta
(74) *Attorney, Agent, or Firm*—Buchanan Ingersoll, PC

(57) ABSTRACT

Submandibular peptides have been isolated and characterised and provide pharmaceutical compositions for the treatment or prevention of anaphylactic reactions, endotoxic reactions and SIRS-induced shock.

28 Claims, 15 Drawing Sheets

OTHER PUBLICATIONS

Kingsnorth et al., "Epidermal growth factor increases tensile strength in intestinal wounds in pigs," *Br. J. Surg.*, 1990, pp. 409-412, vol. 77, John Wiley & Sons, Inc., Chichester, England & NY.

Skinner et al., "Influence of Desalivation on Acid Secretory Output and Gastric Mucosal Integrity in the Rat," *Gastroenterology*, 1981, pp. 335-339, vol. 81, No. 2, WB Saunders, Philadelphia, PA.

Gray et al., "Role of salivary epidermal growth factor in the pathogenesis of Barrett's columnar lined oesophagus," *Br. J. Surg.*, 1991, pp. 1461-1466, vol. 78, John Wiley & Sons, Inc., Chichester, England and New York.

Kurachi et al., "Evidence for the involvement of the submandibular gland epidermal growth factor in mouse mammary tumorigenesis," *Proc. Natl. Acad. USA*, 1985, pp. 5940-5943, vol. 82, National Academy of Sciences, Washington, D.C.

Jones et al., "Epidermal growth factor secreted from the salivary gland is necessary for liver regeneration," *Gastrointest. Liver Physiol.*, 1995, pp. 872-878, vol. 31, The American Physiological Society, Bethesda, Maryland.

Amano et al., "Expression and Localization of Hepatocyte Growth Factor in Rat Submandibular Gland," *Growth Factors*, 1994, pp. 145-151, vol. 10, Harwood Academic Publishers GmbH, Singapore.

Tsutsumi et al., "A physiological Role of Epidermal Growth Factor in male Reproductive Function," *Science*, 1986, pp. 975-977, vol. 233, Amer. Assn. For the Advancement of Science, Washington, D.C.

Tsutsumi et al., "The uterine growth-promoting action of epidermal growth factor and its function in the fertility of mice," *Journal of Endocrinology*, 1993, pp. 437-443, vol. 38, Endocrine Society, Baltimore, MD.

Rosinski-Chupin et al., "The Gene Encoding SMR1, a Precursor-Like Polypeptide of the Male Rat Submaxillary Gland, Has the Same Organization as the Preprothyrotropin-Releasing Hormone Gene," *DNA and Cell Biology*, 1990, pp. 553-559, vol. 9, No. 8, Mary Ann Liebert, Inc, New York, New York.

Rosinski-Chupin et al., "High level of accumulation of a mRNA coding for a precursor-like protein in the submaxillary gland of male rats," *Proc. Natl. Acad. USA*, 1988, pp. 8553-8557, vol. 85, National Academy of Sciences, Washington, D.C.

Kemp et al., "Suppression and enhancement of *in vitro* lymphocyte reactivity by factors in rat submandibular gland extracts," *Immunology*, 1985, pp. 261-267, vol. 56, Elsevier Science, Ltd., England.

Abdelhaleem et al., "Indentification of immunosuppressive fractions from the rat submandibular salivary gland," *Immunology*, 1992, pp. 331-337, vol. 76, Elsevier Science, Ltd., England.

Bissonnette et al., "Decentralization of the Superior Cervical Ganglia Inhibits Mast Cell Mediated TNFα-Dependent Cytotoxicity. 1. Potential Role of Salivary Glands," *Brain, Behavior, and Immunity* 1993, pp. 293-300, vol. 7, Elsevier, Ltd., England.

Carter et al., "Inhibition of neutrophil chemotaxis and activation following decentralization of the superior cervical ganglia," *Journal of Leukocyte Biology*, 1992, pp. 597-602, vol. 51, Society for Leukocyte Biology, Bethesda, Maryland.

Saito et al., "Saliva Inhibits the Chemiluminescence Response, Phagocytosis, and Killing of *Staphylococcus epidermidis* by Polymorphonuclear Leukocytes," *Infection and Immunity*, 1988, pp. 2125-2132, vol. 56, No. 8, American Society for Microbiology, Washington, D.C.

Ramaswamy et al., "Marked Antiinflammatory Effects of Decentralization of the Superior Cervical Ganglia", *Journal of Experimental Medicine*, 1990, pp. 1819-1830, vol. 172, Rockefeller Univ. Press, New York, New York.

Mathison et al., "Role for the Submandibular Gland in Modulating Pulmonary Inflammation following induction of Systemic Anaphylaxis," *Brain, Behavior, and Immunity*, 1992, pp. 117-129, vol. 6, Elsevier Science, Ltd., London, England.

\* cited by examiner

PEPTIDES FOR TREATMENT OF INFLAMMATION AND SHOCK

This application is a divisional of application Ser. No. 09/051,395, filed on May 8, 1998 now U.S. Pat. No. 6,852,697, which is a national stage filing under 35 U.S.C. § 371 of International Application No. PCT/CA97/00568, filed on Aug. 13, 1997, the entire contents of which are incorporated herein in its entirety.

FIELD OF THE INVENTION

This invention relates to peptides which modulate anaphylactic, endotoxic and inflammatory reactions in mammals.

BACKGROUND OF THE INVENTION

In the description which follows, references are made to certain literature citations which are listed at the end of the specification.

Infections, trauma (e.g. falls, automobile accidents, gun and knife wounds), cardiovascular accidents (e.g. aneurysms and ischemic events often associated with surgery) and endogenous inflammatory reactions (e.g. pancreatitis and nephritis) often lead to profound dysfunction of the homeostatic mechanisms involved in regulating cardiovascular and immune system function.

Several conditions such as ischemia and infections, through inappropriate or excessive activation of the immune system, may result in cardiovascular dysfunction that develops over a period of hours to days. Compromised cardiovascular function increases morbidity and is life threatening.

Systemic inflammatory response syndrome (SIRS) is diagnosed largely on observed physiological changes such as increase (fever) or decrease in body temperature (hypothermia), increased heart rate (tachycardia), increased respiration rate (tachypnea), elevated or diminished white blood cell counts and inadequate perfusion of tissues and organs. Changes in blood pressure are not included in the definition because they occur late in the course of the syndrome. Decreases in blood pressure reflect the development of shock, and contribute to multiple organ failure, a leading cause of death in these patients. This definition of sepsis syndrome includes a large number of patients who exhibit similar physiological signals but have no evidence of any type of infection; other insults which induce a sepsis-like condition include pancreatitis, burns, ischemia, multiple trauma and tissue injury (often due to surgeries and transplants), haemorrhagic shock and immune-mediated organ dysfunction.

SIRS is the 13th leading cause of death in the United States of America. On average, 40% of sepsis syndrome patients are dead within 28 days of admission to intensive care.

The standard therapies for SIRS and septic shock involve administration of antibiotics to bring the infection under control and fluid/colloid therapy to maintain circulating blood volume. Frequently, drugs which help maintain blood pressure, such as dopamine and vasopressin, are also administered.

Recent strategies for developing more targeted therapies for the treatment of sepsis have been disappointing. In addition, many molecules in the new generation of anti-septic agents are very expensive and most possibly produce untoward immunological and cardiovascular reactions which make them contra-indicated in some cases of non-bacteremic shock.

Hypersensitivity to environmental antigens can, in severe cases, result in anaphylactic shock, which is treated by the administration of fluids and vasoactive agents to restore blood pressure.

There remains a need for inexpensive and effective agents for treatment of cardiovascular shock, sepsis, systemic inflammatory response syndrome and anaphylaxis.

The salivary glands are classically viewed as accessory digestive glands which mediate their actions through exocrine secretion, although appreciation has grown recently for the importance of their endocrine secretions (1–3). The exocrine secretion of biologically active peptides from the salivary glands is essential for the health of the mouth (4), whereas the endocrine secretions of these glands help maintain the structure and function of a large variety of internal tissues and organs such as the digestive tract (5–7), the mammary glands (8), the liver (9,10), and the reproductive tract (11,12). Rosinski-Chupin et al. (13,14) have described a protein from the male rat submandibular gland which is androgen-regulated and which they believed to have a male-specific function in the rate.

Another important action of salivary endocrine secretions is the modulation of the immune system, with effects being observed on lymphocyte (15,16), mast cell (17) and neutrophil (18,19) functions. The submandibular glands also regulate inflammatory reactions associated with the late-phase pulmonary inflammation induced by allergen in sensitized rats (20–22), and their removal exacerbates the severity of the hypotensive responses induced by intravenously administered lipopolysaccharide (LPS) (23). Removal of the submandibular glands, however, does not affect arterial blood pressure in the normal state (23).

In accordance with one embodiment, the invention provides a peptide of the formula: $R^1$—$X^1$—$X^2$—$R^2$ wherein $X^1$ is an aromatic amino acid residue;

$X^2$ is any amino acid residue;

$R^1$ is $NH_2$— or an amino acid sequence $X^3$—$X^4$—$X^5$
  wherein $X^3$ is an aliphatic amino acid residue having a side chain hydroxyl group and
    $X^4$ and $X^5$ are the same or different and are any amino acid residue and wherein $R^2$ is a sequence of 1 to 3 amino acid residues which are the same or different and are aliphatic amino acid residues.

In accordance with a further embodiment, the invention provides a peptide having the amino acid sequence
Ser-Gly-Glu-Gly-Val-Arg (Sequence ID NO:1).

In accordance with a further embodiment, the invention provides a method for treating or preventing SIRS-induced hypotension in a mammal comprising administering to the mammal an effective amount of a described peptide or of an effective fragment or derivative of the peptide.

In accordance with a further embodiment, the invention provides a method for treating or preventing anaphylactic hypotension in a mammal comprising administering to the mammal an effective amount of a described peptide or of an effective fragment or derivative of said peptide.

In accordance with a further embodiment, the invention provides a method of reducing or preventing an anaphylactic reaction in a mammal comprising administering an effective amount of a described peptide or of an effective fragment or derivative of said peptide to the mammal.

In accordance with a further embodiment, the invention provides a method of reducing or preventing an endotoxic reaction in a mammal comprising administering an effective amount of a described peptide or 11 or an effective fragment or derivative of said peptide to the mammal.

In accordance with a further embodiment, the invention provides a method for treating an inflammatory disorder in a mammal comprising administering to the mammal an effective amount of a described peptide or of an effective fragment or derivative of the peptide to the mammal.

In accordance with a further embodiment, the invention provides an antibody which specifically recognises an epitope of a peptide of the invention.

In accordance with a further embodiment, the invention provides a method of determining the peptide SGP-T or the peptide SGPS in a biological fluid comprising obtaining a sample of the biological fluid and determining the peptide in the fluid by immunoassay employing an antibody which specifically epitope of a peptide of the invention.

Certain embodiments of the invention are described, reference being made to the accompanying drawings, wherein.

A: no drug
B: 10 µg SGP-T
C: 35 µg SGP-T
D: 100 µg SGP-T. * p<0.05

Figure 3:
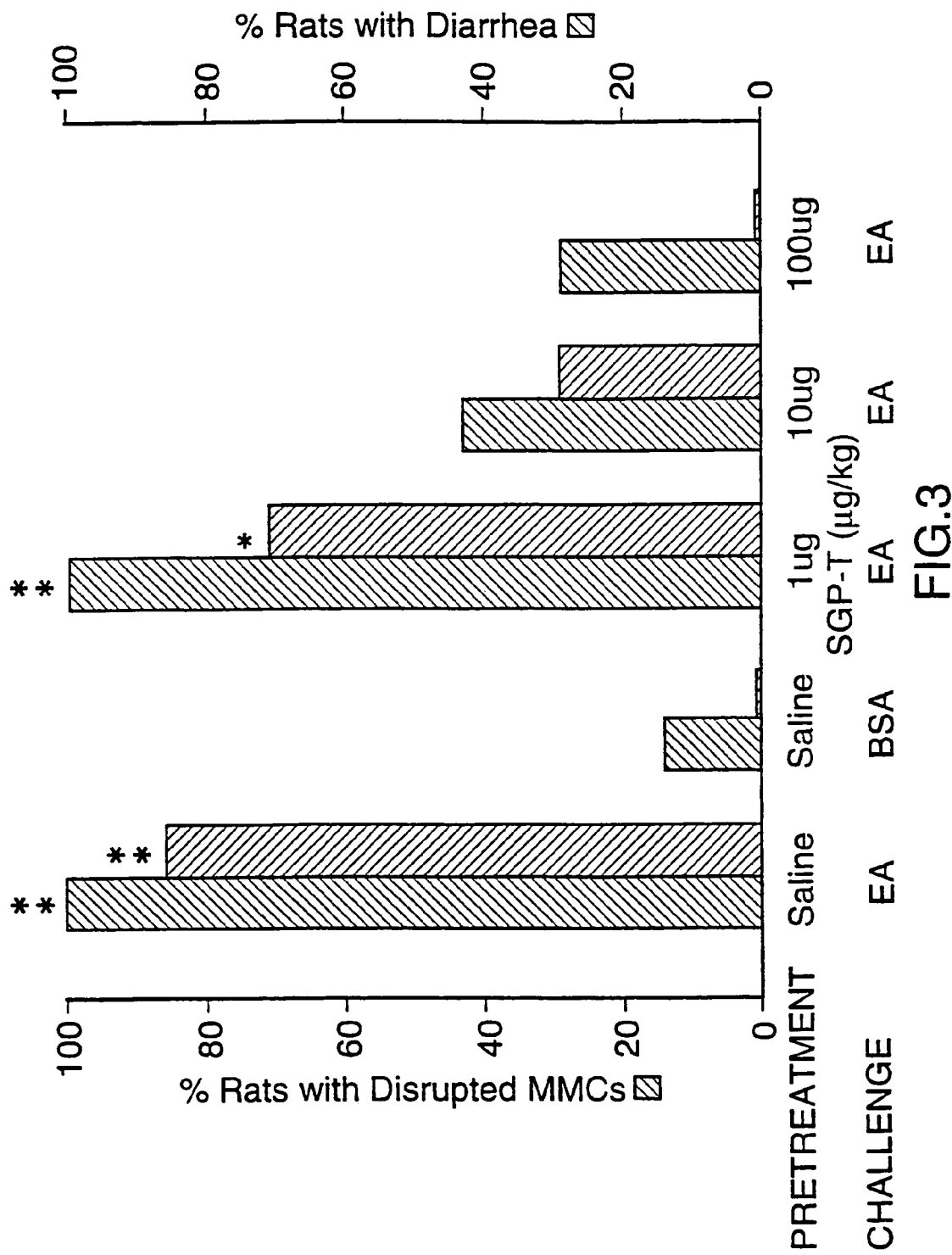

FIG. 3 shows % treated rats with disrupted MMC's (solid bars) or diarrhoea (hatched bars) after the indicated pretreatments, followed by challenge with egg albumin (EA) or bovine serum albumin (BSA).

Figure 4:
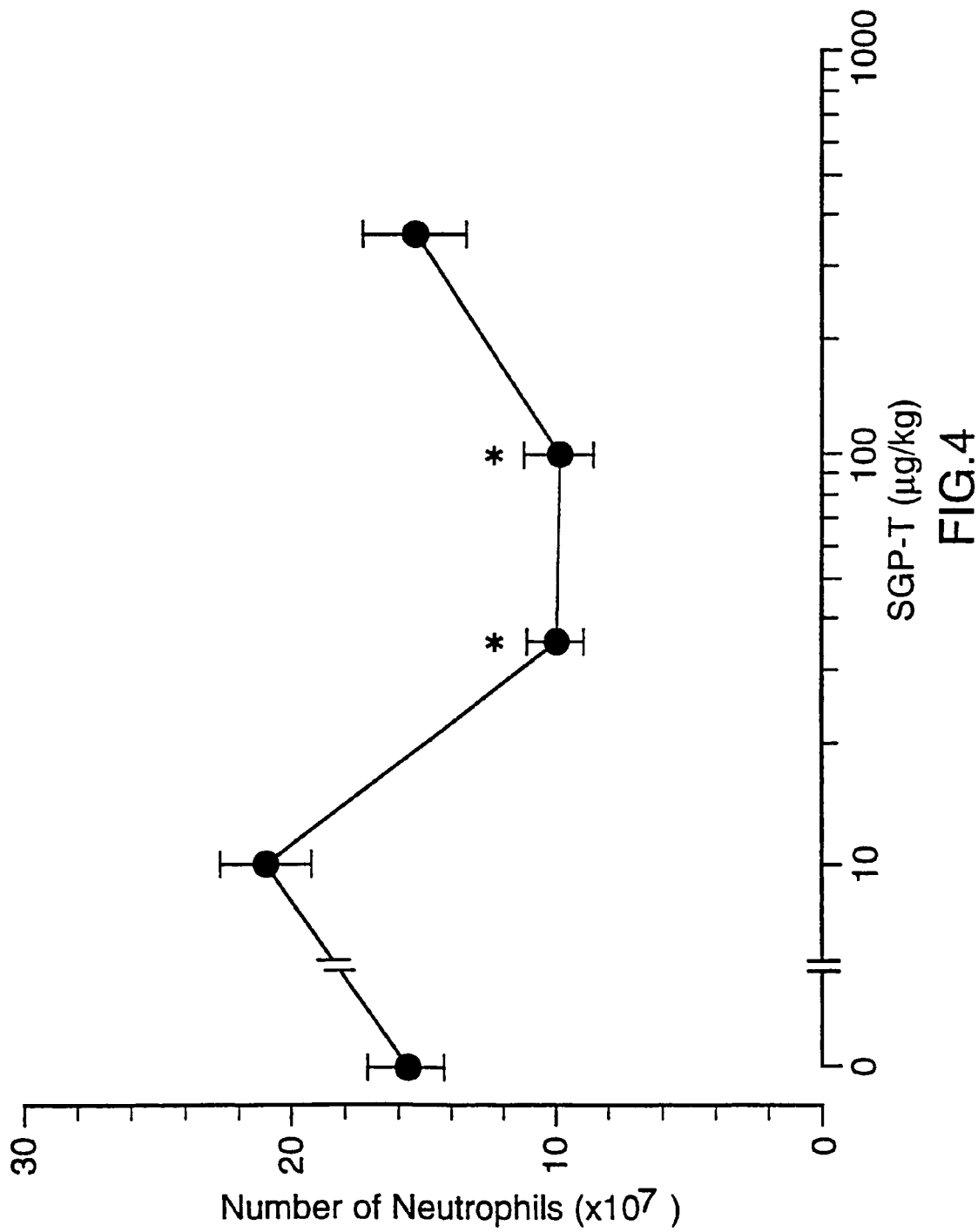

FIG. 4 shows number of neutrophils migrating into carrageenin-soaked sponges implanted in rats treated with various indicated concentrations of SGP-T.

Figure 5:
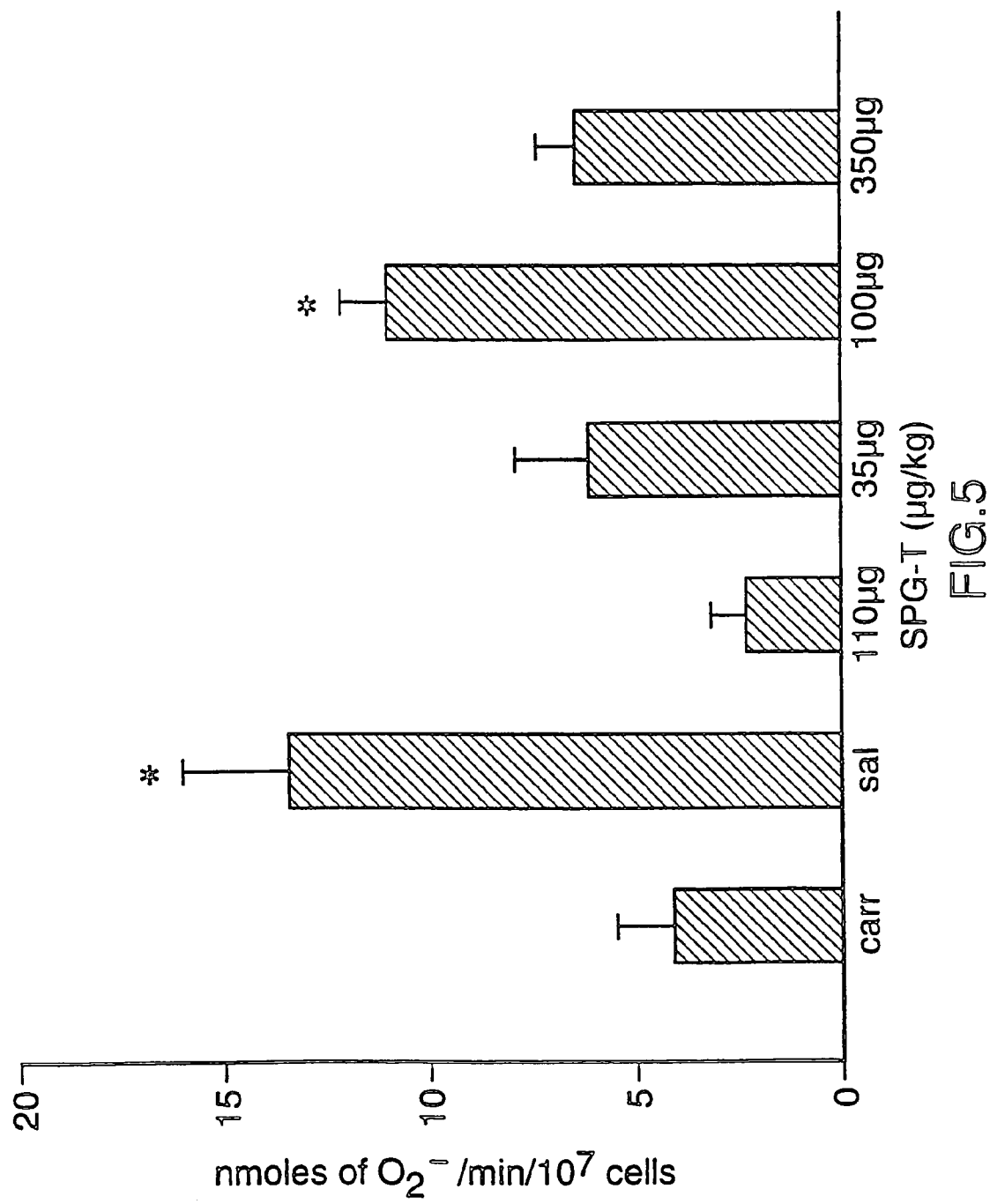

FIG. 5 shows superoxide anion production, expressed as n moles $O_2^-/min/10^7$ cells, in neutrophils from carrageenin-soaked sponges implanted in rats treated with various indicated concentrations of SGP-Tcarr=carrageenin-soaked sponge from rat with no SGP-T treatment; sal=saline soaked sponge (control) from rat with no SGP-T treatment.

Figure 6:
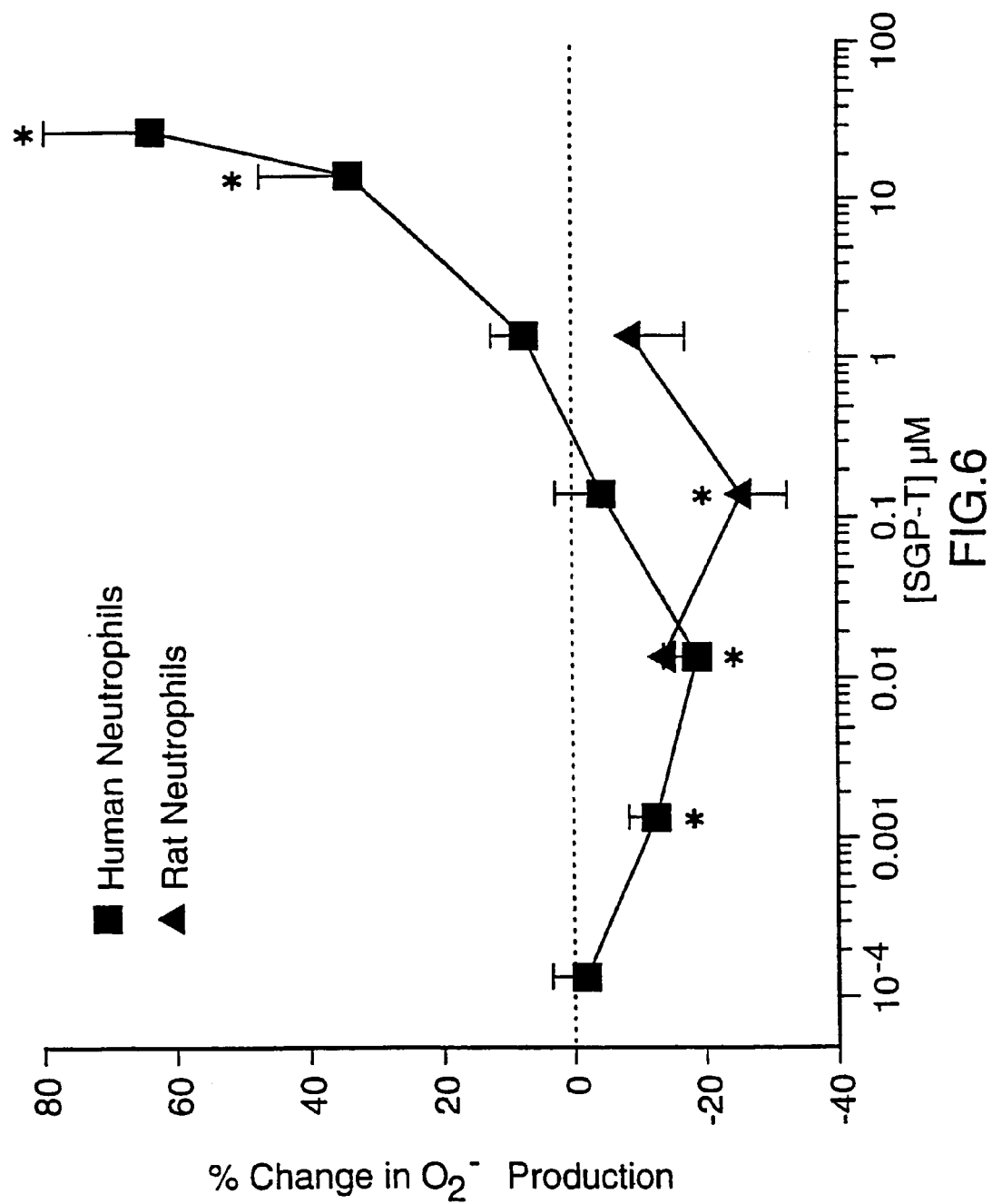

FIG. 6 shows superoxide anion production by human (■) or rat (▲) neutrophils treated in vitro with SGP-T.

Figure 7:
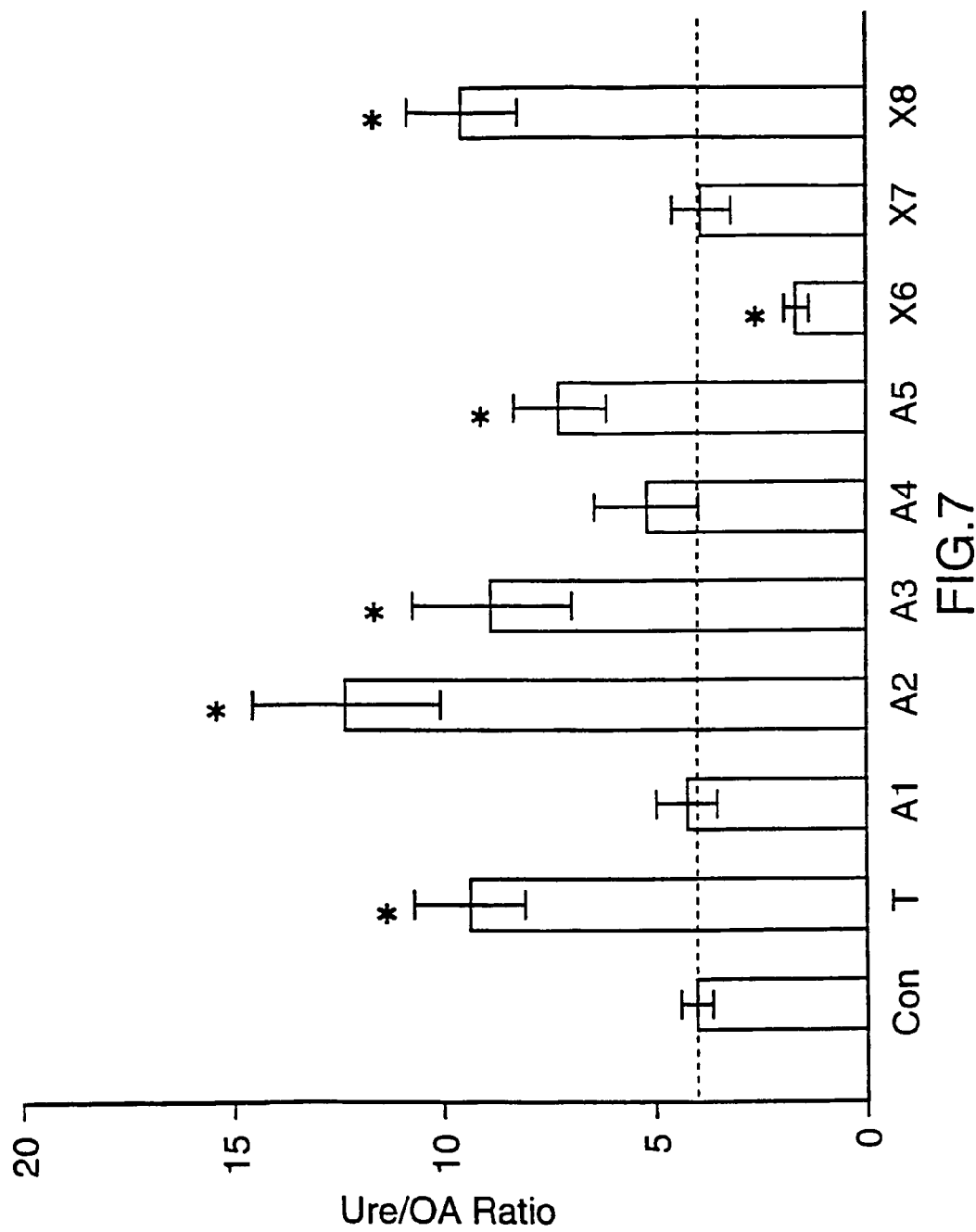

FIG. 7 shows the effect of SGP-T and various analogues and fragments on antigen-induced jejunal segment contraction (from ovalbumin (OA)- sensitized rats). Con: saline control; T: SGP-T; A1: ADIFEGG (Sequence ID NO:2); A2 (Sequence ID NO:3): TAIFEGG (Sequence ID NO:3); A3: TDAFEGG (Sequence ID NO:4); A4: TDIAEGG (Sequence ID NO:5); A5: TDIFAGG (Sequence ID NO:6); X6: TDIFE (Sequence ID NO:7); X7: TDIFEGG-NH2 (Sequence ID NO:8); X8: FEGGG (Sequence ID NO:9). Ure/OA Ratio (X axis) is the ratio of the contractile response to the cholinergic agonist, urecholine (URE), divided by the contractile response to OA. * P<0.05. The dotted line indicates the control (Con) response across the figure.

Figure 8:
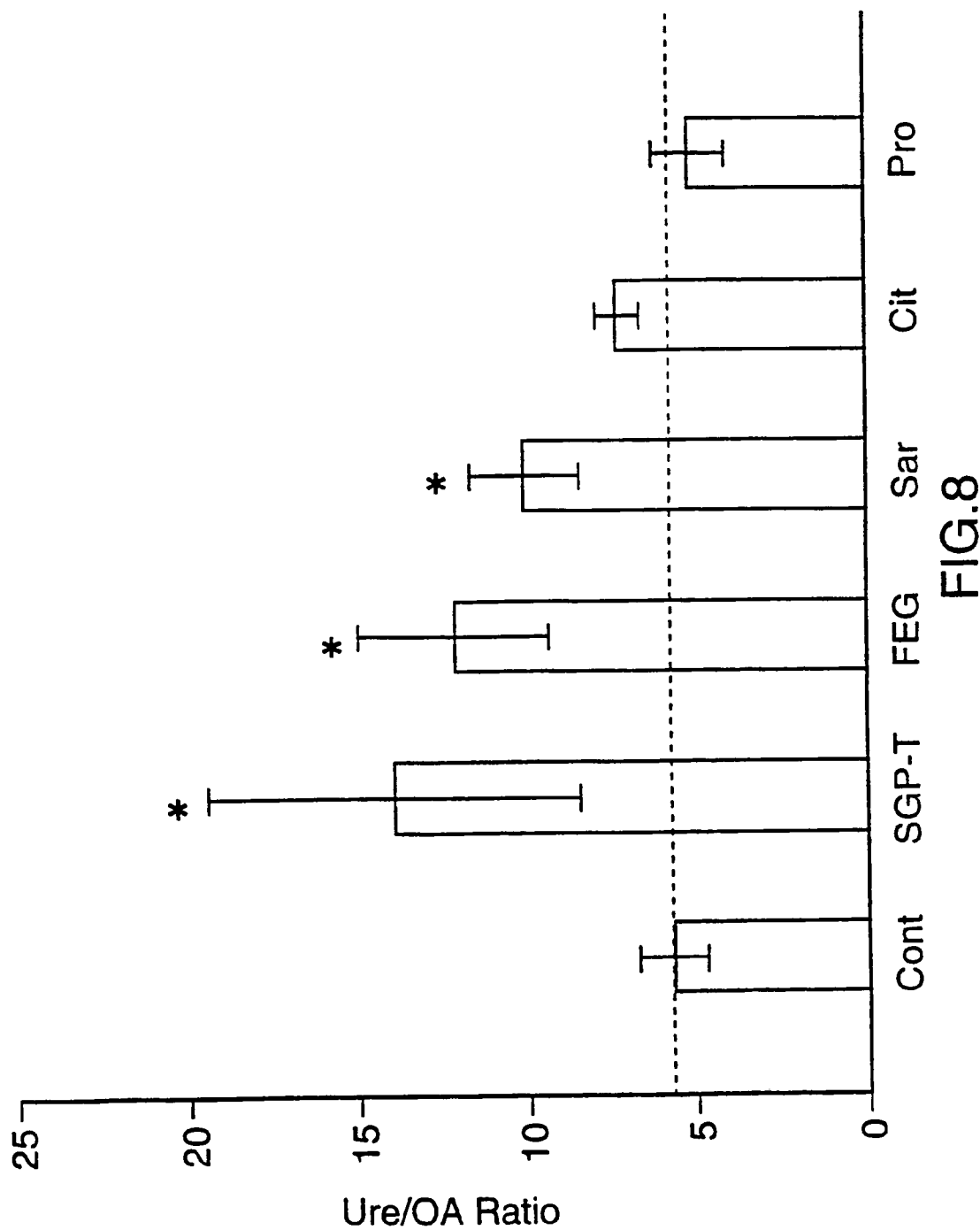

FIG. 8 shows the effect of SGP-T and various analogues on antigen-induced jejunal segment contraction (from OA-sensitized rats). Cont: control; T: SGP-T; FEG: FEG; Sar: FE-Sarcosine; CIT: FE-Citrulline; Pro: FE-proline. Ure/OA Ratio (X axis) is the ratio of the contractile response to the cholinergic agonist, urecholine (URE), divided by the contractile response to OA. * P<0.05. The dotted line indicates the control (Con) response across the figure.

Figure 9:
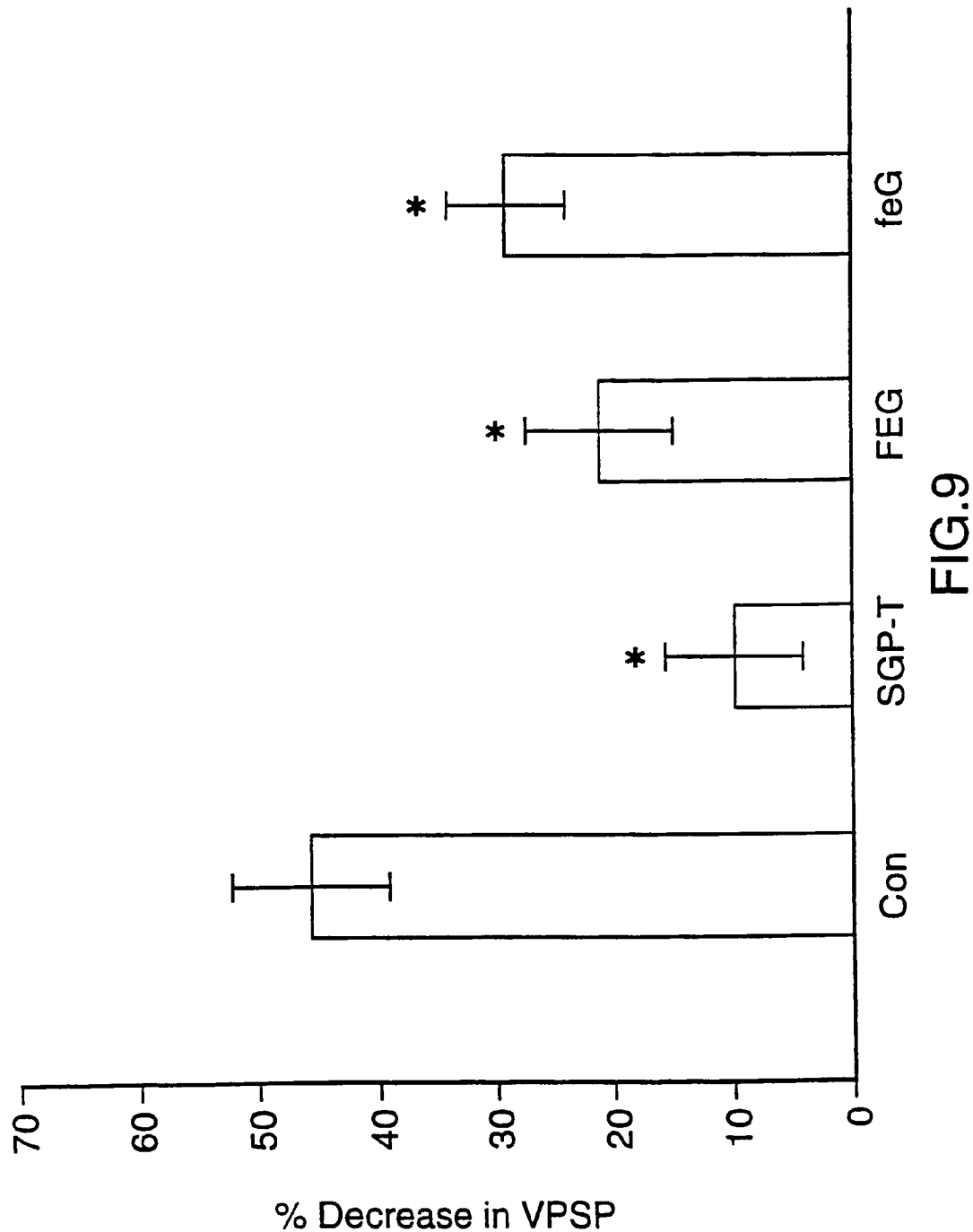

FIG. 9 shows the effect of SGP-T and various analogues on antigen-induced anaphylactic hypotension. X axis: ventricular peak systolic pressure (VPSP). Con saline control; feG: D-phenylalanine, D-glutamate, glycine. * P<0.05

Figure 10:
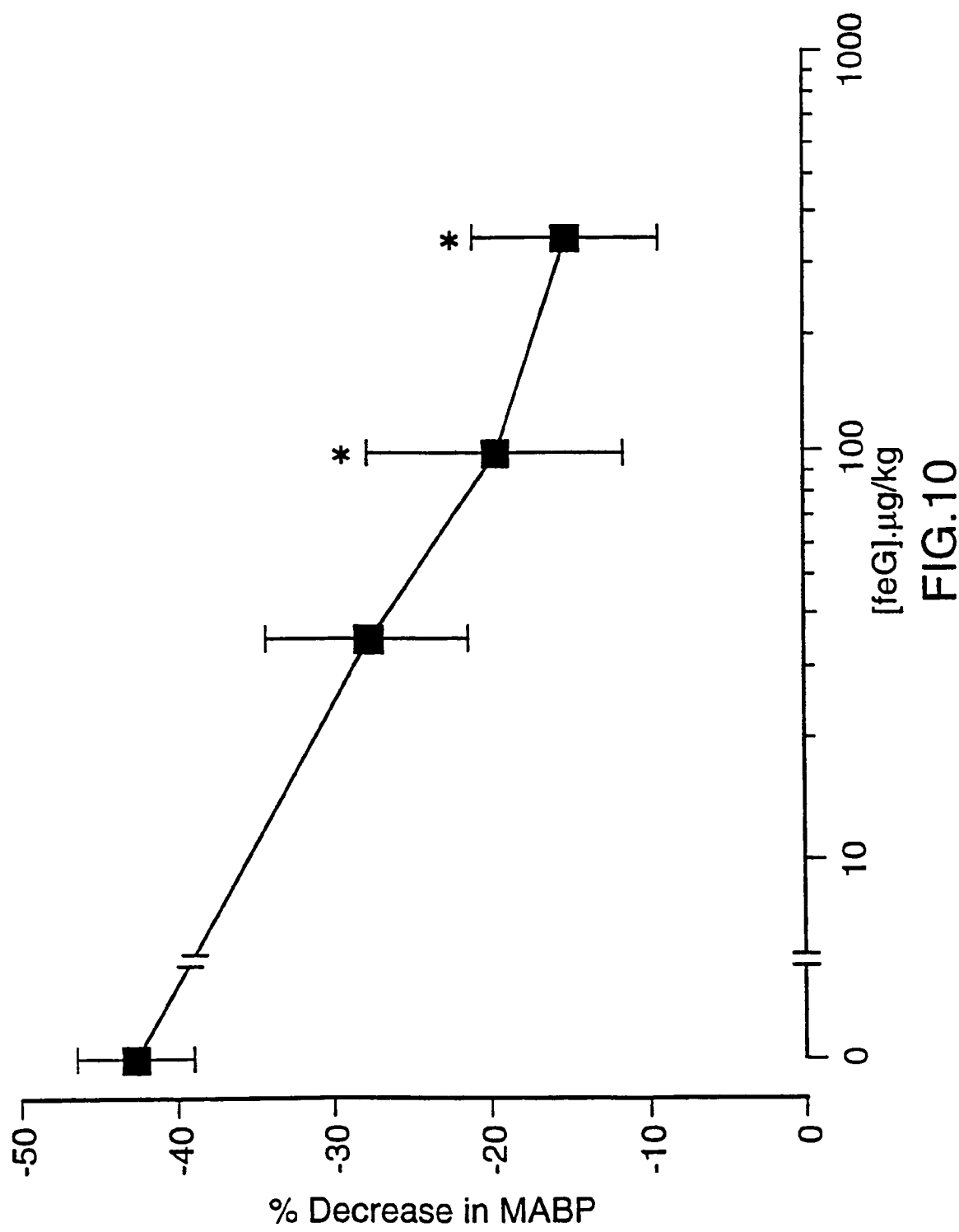
Figure 11:
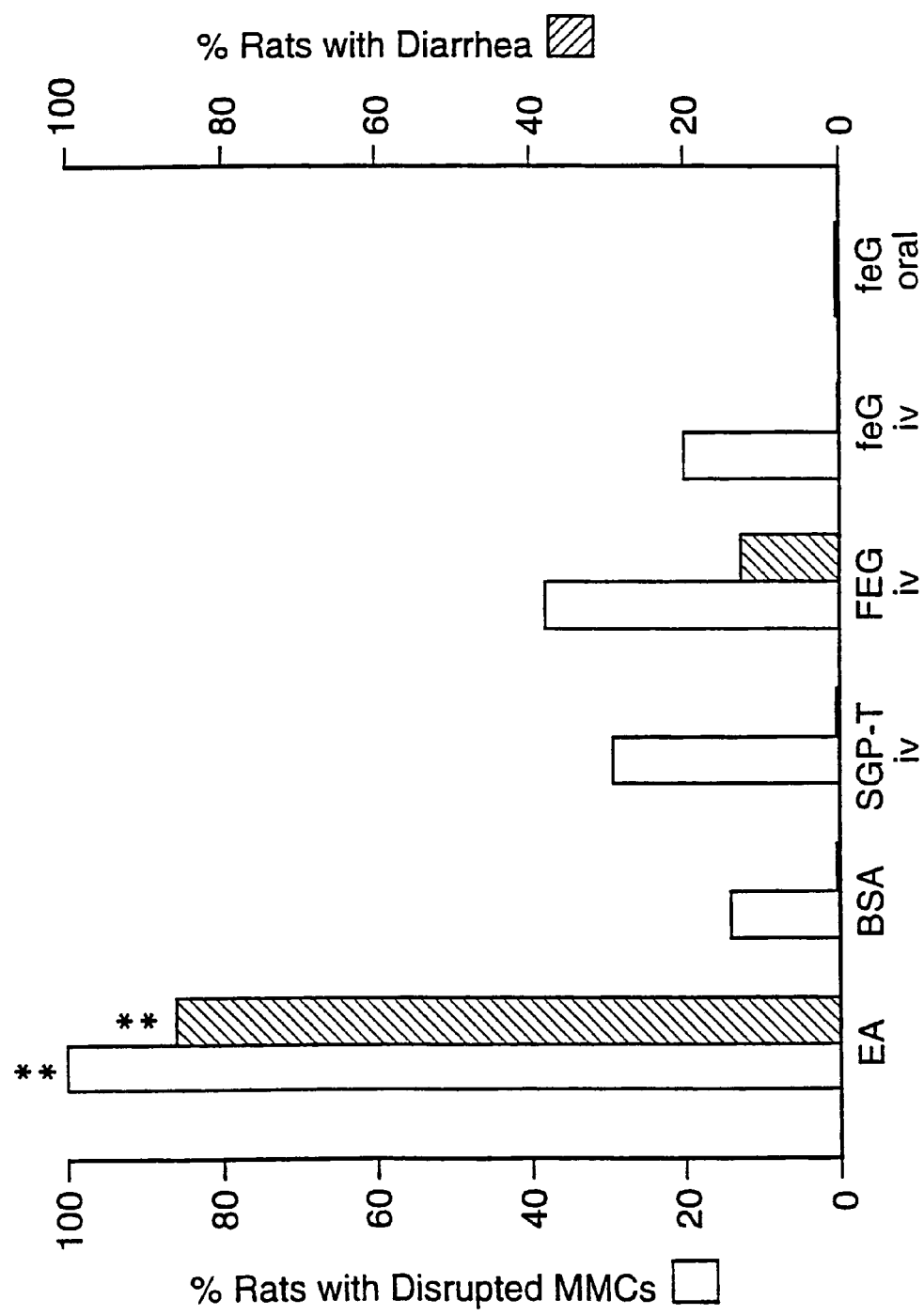

FIG. 10 shows the effect of feG on antigen-induced anaphylactic hypotension. X axis: VPSP FIG. 11 shows the incidence of disrupted intestinal myoelectric activity (disrupted MMC's) and diarrhoea in rats treated with egg albumin alone (EA), bovine serum albumin alone (BSA), SGP-T prior to OA (SGP-T), FEG prior to OA (FEG), feG prior to OA (feG) and feG orally prior to OA (feG oral).

Figure 12:
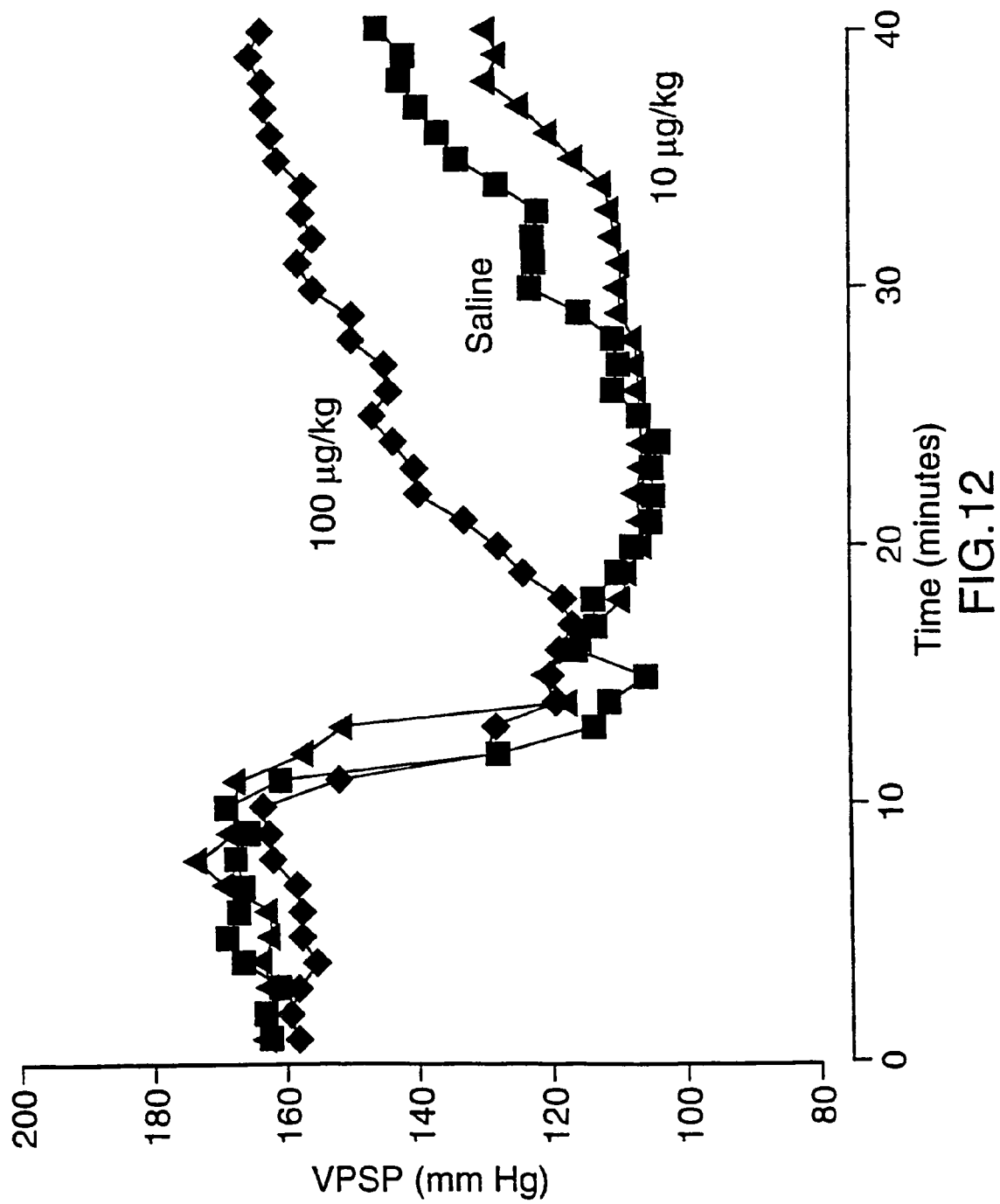

FIG. 12 shows changes in ventricular peak systolic pressure (VPSP) over time in rats treated with saline (■), 10 µg/kg SGP-T (▲) or 100 µg/kg SGP-T (♦) prior to challenge with antigen. * P<0.05, n≧4

Figure 13:
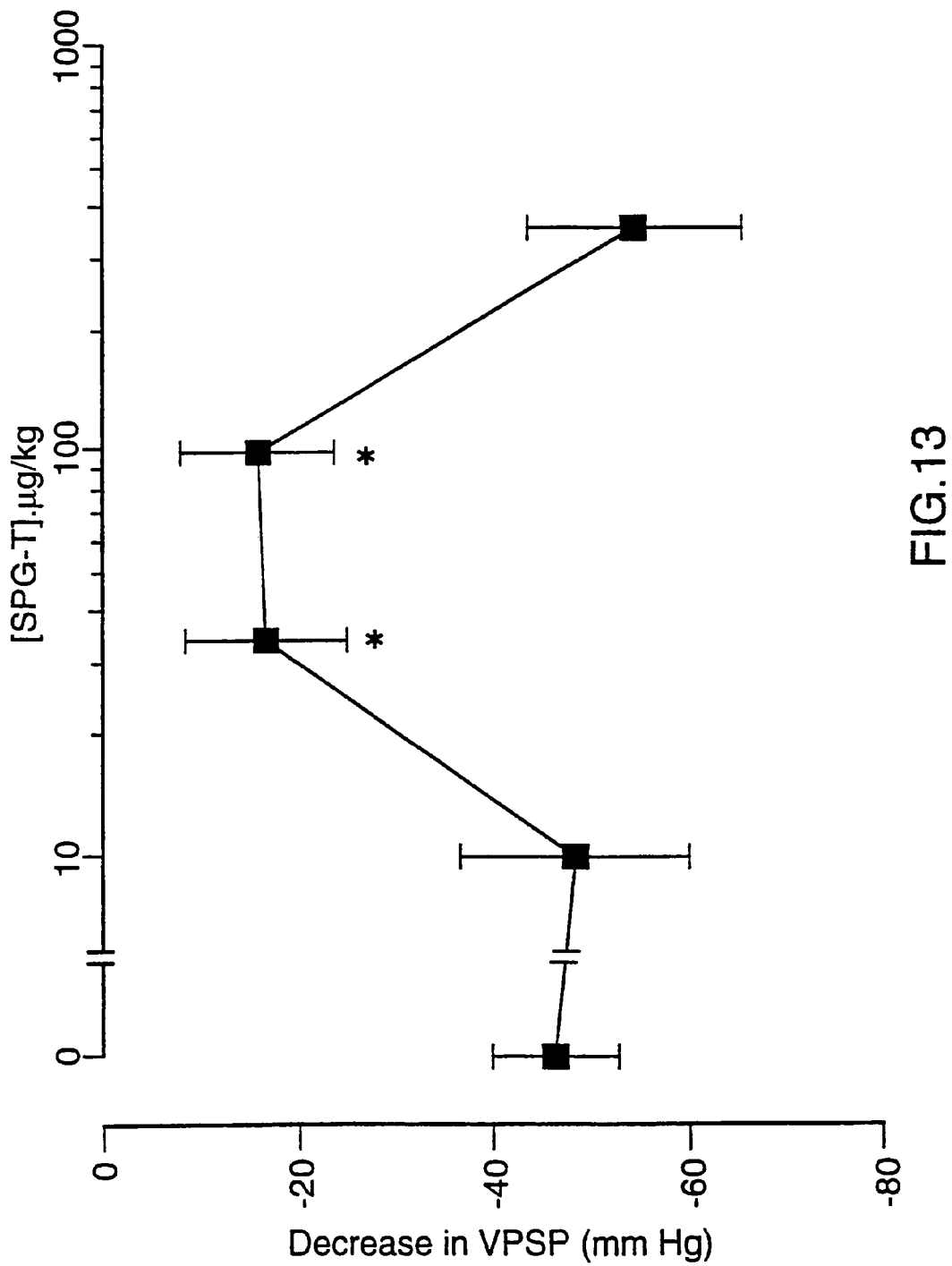

FIG. 13 shows the antigen-induced decrease in VPSP in rats after pre-treatment with various doses of SGP-T. * P<0.05.

Figure 14:
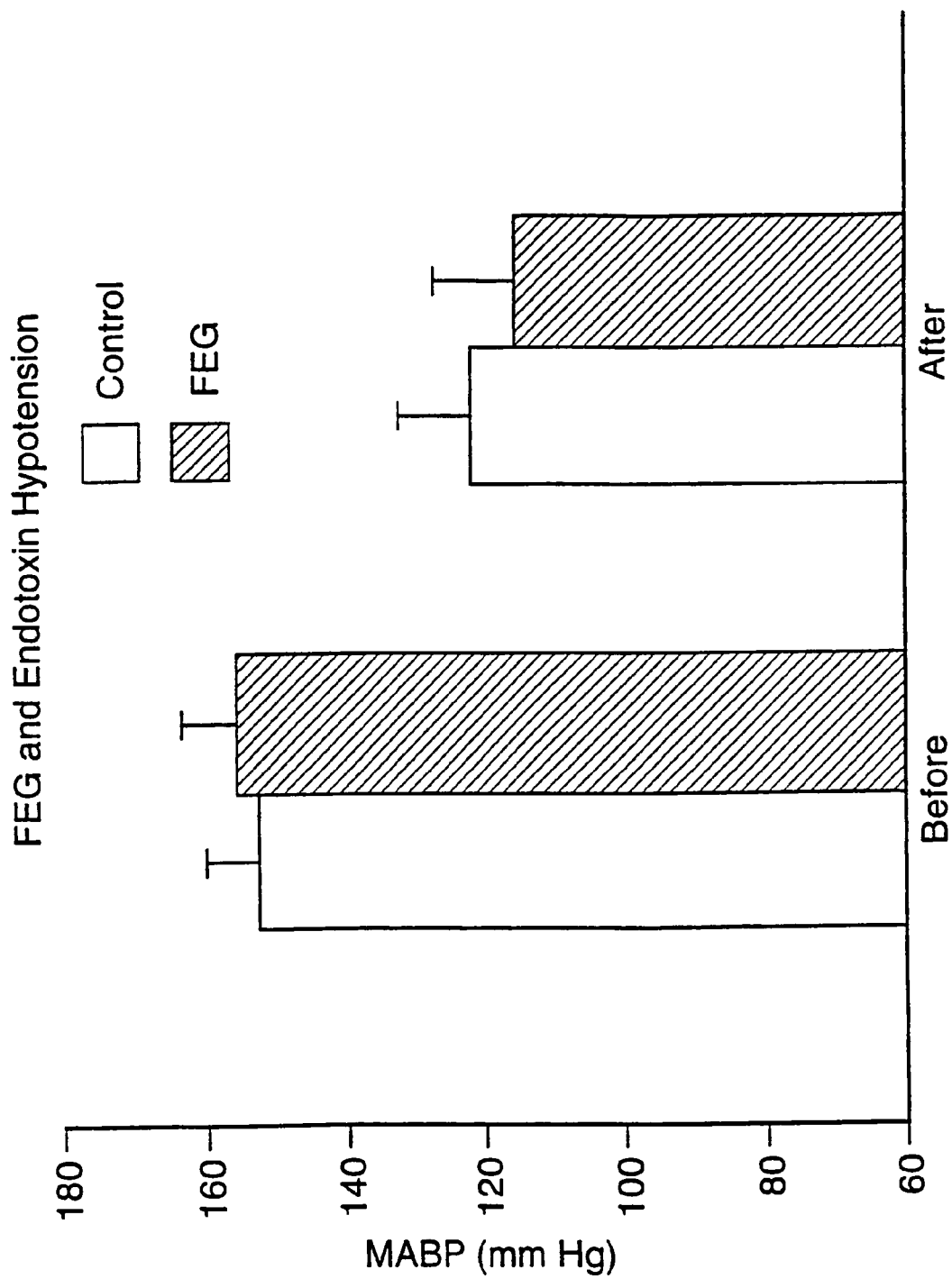

FIG. 14 shows MABP 10 min before (Before) or 60 minutes after (After) LPS injection in rats treated 30 minutes before LPS with FEG (hatched bars) or vehicle (open bars).

Figure 15:
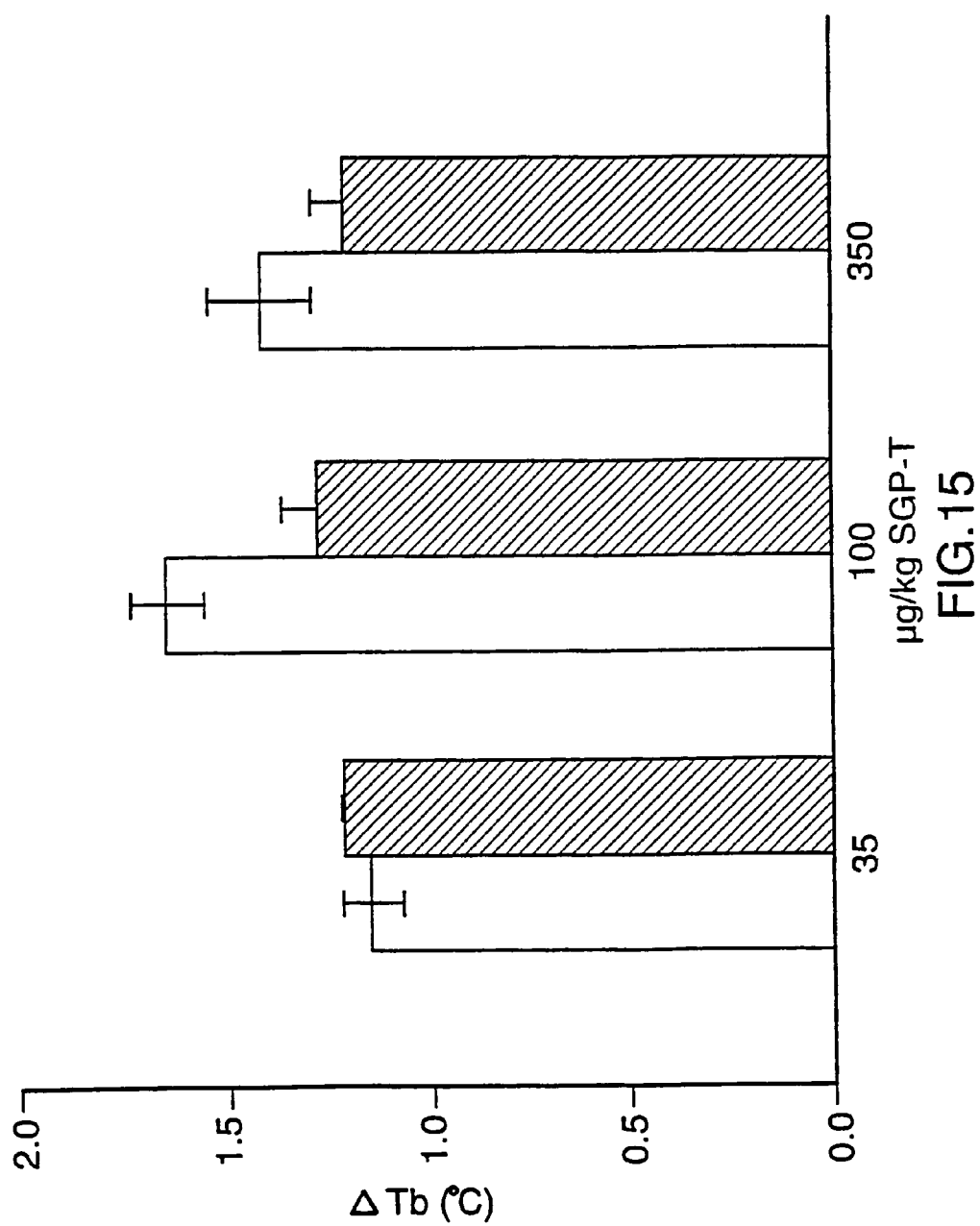

FIG. 15 shows the effect of SGP-T at various concentrations (solid bars) on endotoxin-induced fever (X axis: ΔTb=change in body temperature (° C.)) relative to pre-endotoxin body temperaturs. Open bars: control * P<0.05 n=4.

DETAILED DESCRIPTION OF THE INVENTION

The present invention relates to peptides obtained from mammalian submandibular glands which modulate anaphylactic reactions and endotoxic and inflammatory reactions in mammals.

Anaphylactic reactions in mammals are severe and harmful reactions to an allergen to which a mammal has become sensitized or hypersensitized. These reactions are severe or excessive manifestations of an immunological protective mechanism designed to protect the mammal against foreign antigens. Anaphylactic reactions can occur in response to such allergens as insect bites and stings, plant pollens, plants such as poison ivy, food allergens, such as nuts and seafood, animal dander and house dust and have a role in the etiology of asthma, rhinitis, urticaria, eczema and certain gastrointestinal disorders.

An anaphylactic reaction to an antigen can be associated with hypotension, increased intestinal motility, diarrhea, bronchial constriction and edematous swelling. Anaphylactic hypotension may be severe enough to cause anaphylactic shock, which may be life-threatening.

Endotoxic reactions in mammals develop consequent to the activation of the immune system in an attempt to rid the body of a bacterial infection. Unlike anaphylactic reactions, which develop rapidly in a matter of minutes, endotoxic reactions increase in severity over a period of days. Pro-inflammatory mediators such as cytokines, which are released as part of the body's response to an infection, stimulate the respiratory and cardiovascular systems. In some patients, the fight against the infection fails and the pro-inflammatory mediators begin to have deleterious effects on the patient, promoting the progressive collapse of the cardiovascular system, poor organ perfusion and further tissue damage. If these severe inflammatory reactions are not arrested, endotoxic shock can ensue.

A clinically useful paradigm has been developed that helps define patients that could possibly progress into sepsis or sepsis-like conditions, and eventually shock. This paradigm is called the systemic inflammatory response syndrome (SIRS).

SIRS is defined clinically as the presence of two or more of the following criteria:

1) a body temperature greater than 38° C. or less than 36° C.;
2) a heart rate greater than 90 beats/minute;
3) a respiratory rate greater than 20 breaths/minute;
4) a white blood cell count greater than 12 million/ml or less than 4 million/ml.

Some 68% of all patients entering the hospital possess SIRS, and thus are at risk for the development of sepsis or a sepsis-like condition and shock. A confirmed infectious process (i.e. positive blood cultures) are required for the rigorous diagnosis of sepsis. Nonetheless, some infection-negative patients progress to a stage of severe sepsis, which is defined by the presence by one of the following conditions:

1) a reduction of systolic blood pressure to less than 90 mm Hg;
2) a systemic manifestation of poor tissue perfusion as reflected by lactic acidosis, low urine output or acute alteration of mental state.

An SIRS patient can progress directly to severe sepsis, in the absence of a definable infectious agent. Some of the conditions that favour progression to the severe sepsis stage include: pancreatitis, burns, and cerebral or spinal injuries. Patients with SIRS can proceed to SIRS-induced hypotension and SIRS-induced shock. A patient is considered to be in shock if he or she remains hypotensive (i.e. systolic blood pressure below 90 mm Hg) following the administration of 500 ml of fluid.

The cervical sympathetic trunk-submandibular gland (CST-SMG) axis has recently been identified as a neuroendocrine axis that modulates pulmonary inflammatory and cardiovascular responses provoked by sensitizing antigen (20,21) and endotoxins (23), respectively. The cervical sympathetic nerves modulate such. inflammatory reactions, for example that induced by intravenous administration of gram negative bacterial endotoxin, by regulating the release, from the submandibular glands (3), of factors which reduce the severity of the reaction (23).

The present inventors have obtained from rat submandibular glands, and characterized, two novel peptides which have profound effects on a variety of cardiovascular and immunological perturbations and are likely candidates for the agents by which the submandibular gland exerts its influence on anaphylactic or endotoxic reactions.

In accordance with one embodiment, the present invention provides submandibular gland peptides S and T (SGP-S and SGP-T), which have the following amino acid sequences:

SGP-S:  $NH_2$-Ser-Gly-Glu-Gly-Val-Arg-COOH (SGEGVR: Sequence ID NO:1);
SGP-T:  $NH_2$-Thr-Asp-Ile-Phe-Glu-Gly-Gly-COOH (TDIFEGG Sequence ID NO:8).

The invention also includes effective fragments and derivatives of these peptides which retain at least one biological activity of the peptide from which they are derived. The terms "derivative" extends to any functional and/or chemical equivalent of the peptides of the invention and includes peptides having one or more amino acid substitutions, peptides incorporating unnatural amino acids and peptides having modified side chains. The invention also includes homologues of these peptides in other species, including human. Such homologues may be identified using antibodies to the peptides disclosed herein, as will be understood by those of ordinary skill in the art.

The biological effects of SGP-T include reduction or prevention of endotoxic hypotension, at doses as low as 1 μg peptide/kg body weight; reduction or prevention of anaphylactic hypotension in foreign protein-sensitised mammals; a protective effect against ventricular dysfunction during systemic anaphylaxis; attenuation of antigen-induced perturbations of gastrointestinal motility in ovalbumin-sensitised animals; a significant reduction of in vitro antigen-induced smooth muscle contraction, in muscle from ovalbumin-sensitized animals; a significant reduction of the fever provoked by bacterial endotoxin; an approximately 50% inhibition of neutrophil migration; a prevention of carrageenin-induced inhibition of superoxide production by phorbal myristate (PMA) and formyl-Met-Leu-Phe. (fMLP);

The invention enables pharmaceutical compositions comprising the peptide SGP-T or an effective fragment or derivative thereof, for the treatment or prevention of anaphylactic reactions, including anaphylactic shock, and endotoxic reactions, including endotoxic shock.

These compositions may also be used for the treatment or prevention of systemic inflammatory response syndrome (SIRS) and the treatment of inflammation or any disorder ameliorated by down regulation of neutrophil function. Such disorders include rheumatic diseases, inflammatory bowel disease and post-ischemic lesions subsequent to stroke or cardiac infarct.

The peptides of the invention modulate and reduce the severity of anaphylactic reactions, including cardiovascular and intestinal anaphylactic reactions, anaphylactic shock and SIRS-induced reactions, including endotoxic shock and SIRS-induced shock.

The invention also enables methods for preventing or treating anaphylactic reactions, including anaphylactic shock, endotoxic reactions, including endotoxic shock, SIRS, inflammation and disorders ameliorated by down regulation of neutrophil function.

Examination of fragments and derivatives of SGP-T indicates that various amino acid substitutions may be effected without loss of biological activity, as shown in Tables 2, 3 and 4.

SGP-T and various full length derivatives thereof are active in inhibiting anaphylactic and endotoxic hypotension.

The fragment FEG shows the same activity as SGP-T in inhibiting anaphylactic hypotension but does not inhibit endotoxic hypotension. The anti-anaphylactic hypotension activity of FEG is maintained if D amino acids are substituted for F and G.

Although the mechanism of action of the peptides of the invention is still unknown, these results suggest that the anti-endotoxic activity and the anti-anaphylactic activity of SGP-T may be mediated by different cell receptors.

SGP-T does not prevent an initial anaphylactic reaction (see FIG. 12 which shows the same initial blood pressure drop in SGP-T-treated animals and controls) but it does prevent a sustained anaphylactic reaction. This later-phase inhibitory effect could occur by one or both of two mechanisms: 1) prevention of the release of mediators whose synthesis is stimulated by the binding of the allergen to the immunoglobulin E receptors on mast cells. Such mediators include leukotrienes, platelet activating factor and prostaglandins; 2) prevention of the reaction of either the preformed or the newly formed mediators with effector cells contributing to the hypotension or disturbances in intestinal motility. Practice of the invention is not, however, dependent on the mechanism by which these peptides act.

The invention also enables methods for preventing and/or treating inflammation, anaphylactic reactions, including anaphylactic shock, endotoxic reactions including endotoxic shock, and SIRS, by administration of an effective amount of SGP-T or an effective fragment or derivative thereof.

The invention further enables pharmaceutical compositions comprising the peptide SGP-S or an effective fragment or derivative thereof, for the treatment or prevention of endotoxic reactions, including endotoxic shock.

The invention also enables methods for preventing or treating endotoxic reactions, including endotoxic shock, by administration of an effective amount of the peptide SGP-S or of an effective fragment or derivative thereof.

Peptides SGP-T and SGP-S and effective fragments or derivatives thereof may be administered prophylactically to patients at risk of developing shock before they progress into shock, or may be administered after shock has developed, to combat hypotension.

Peptide SGP-T and effective fragments or derivatives thereof may be administered prophylactically to prevent anaphylactic reactions in susceptible subjects, for example individuals who experience anaphylactic reactions to insect bites or stings, to pollens, to particular foods or to occupational allergens such as grain dusts or latex, or used to arrest the progression of an already initiated anaphylactic reaction to a more severe or more systemic reaction.

Preparation of Peptides

Peptides in accordance with the invention or fragments or derivatives thereof may be prepared by any suitable peptide synthetic method.

Chemical synthesis may be employed, for example standard solid phase peptide synthetic techniques may be used. In standard solid phase peptide synthesis, peptides of varying length can be prepared using commercially available equipment. This equipment can be obtained, for example, from Applied Biosystems (Foster City, Calif.). The reaction conditions in peptide synthesis are optimized to prevent isomerization of stereochemical centres, to prevent side reactions and to obtain high yields. The peptides are synthesized using standard automated protocols, using t-butoxycarbonyl-alpha-amino acids, and following the manufacturer's instructions for blocking interfering groups, protecting the amino acid to be reacted, coupling, deprotecting and capping of unreacted residues. The solid support is generally based on a polystyrene resin, the resin acting both as a support for the growing peptide chain, and as a protective group for the carboxy terminus. Cleavage from the resin yields the free carboxylic acid. Peptides are purified by HPLC techniques, for example on a preparative C18 reverse phase column, using acetonitrile gradients in 0.1% trifluoroacetic acid, followed by vacuum drying.

Peptides may also be produced by recombinant synthesis. A DNA sequence encoding the desired peptide is prepared and subcloned into an expression plasmid DNA. Suitable mammalian expression plasmids include pRC/CMV from Invitrogen Inc. The gene construct is expressed in a suitable cell line, such as a Cos or CHO cell line and the expressed peptide is extracted and purified by conventional methods. Suitable methods for recombinant synthesis of peptides are described in "Molecular Cloning" (25). Derivatives of a peptide may be prepared by similar synthetic methods. Examples of side chain modifications contemplated by the present invention include modification of amino groups such as by reductive alkylation by reaction with an aldehyde followed by reduction with $NaBH_4$; amidation with methylacetimidate; acetylation with acetic anhydride; carbamylation of amino groups with 2, 4, 6, trinitrobenzene sulfonic acid (TNBS); alkylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3-butanedione, phenylglyoxal and glyoxal.

The carboxyl group may be modified by carbodiimide activation via acylisourea formation followed by subsequent derivatization, for example, to a corresponding amide.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid-, t-butyglycine, norvaline, phenylglycine, ornithine, sarcosine, 4-amino-3-hydroxy-6-methylheptanoic acid, 2-thienyl alanine and/or D-isomers or amino acids.

Examples of conservative amino acid substitutions are substitutions within the following five groups of amino acids:

Group 1: F Y W
Group 2: V L I
Group 3: HKR
Group 4: M S T P A G
Group 5: D E

Fragments or derivatives of the peptides of the invention may be screened for their effectiveness by one of the assay systems described herein. The assay selected will depend on the biological activity of interest in each case. For example, peptide fragments or derivatives may be screened for their effectiveness in inhibiting intestinal anaphylaxis by the method described in Example 7 or for their effectiveness in inhibiting endotoxic hypotension by the method described in Example 2.

The peptides of the invention may be administered therapeutically by injection or by oral, nasal, buccal, sub-lihgual, rectal, vaginal, transdermal or ocular routes in a variety of formations, as is known to those in the art.

For oral administration, various techniques can be used to improve stability, based for example on chemical modification, formulation and use of protease inhibitors. Stability can be improved if synthetic amino acids are used, such as peptides or betidamino acids, or if metabolically stable analogues are prepared.

Formulation may be, for example, in water/oil emulsion or in liposomes for improved stability. Oral administration of peptides may be accompanied by protease inhibitors such as aprotinin, soybean trypsin inhibitor or FK-448, to provide protection for the peptide. Suitable methods for preparation of oral formulations of peptide drugs have been described, for example, by Saffran et al., (26), (use of trasylol protease inhibitor); Lundin et al. (27) and Vilhardt et al., (28).

Due to the high surface area and extensive vascular network, the nasal cavity provides a good site for absorption of both lipophilic and hydrophilic drugs, especially when coadministered with absorption enhancers. The nasal absorption of peptide-based drugs can be improved by using aminoboronic acid derivatives, amastatin, and other enzyme inhibitors as absorption enhancers and by using surfactants such as sodium glycolate, as described in Amidon et al., (29).

The transdermal route provides good control of delivery and maintenance of the therapeutic level of drug over a prolonged period of time. A means of increasing skin permeability is desirable, to provide for systemic access of peptides. For example, iontophoresis can be used as an active driving force for charged peptides or chemical enhancers such as the nonionic surfactant n-decylmethyl sulfoxide (NDMS) can be used.

Transdermal delivery of peptides is described in Amidon et al. (29) and Choi et al. (30).

Peptides may also be conjugated with water soluble polymers such as polyethylene glycol, dextran or albumin or incorporated into drug delivery systems such as polymeric matrices to increase plasma half-life.

More generally, formulations suitable for particular modes of administration of peptides are described, for example, in Remington's Pharmaceutical Sciences (31).

The particular dosage required in a given subject can be determined by the attending physician. A starting dosage in the range of 1 µg peptide/kg body weight to 100 µg/kg can be employed, with adjustment of the dosage based on the response of a particular subject, as understood by those of ordinary skill in the art.

Antibodies

The peptides of the invention may be coupled to a carrier protein to increase immunogenicity for antibody production. For example, the peptides of the invention may be coupled to bovine serum albumin or keyhole limpet haemocyanin.

In order to prepare peptides for production of polyclonal antibodies, fusion proteins containing a selected peptide, such as peptide 15 or peptide 42, can be synthesized in bacteria by expression of corresponding DNA sequences in a suitable cloning vehicle. Fusion proteins are commonly used as a source of antigen for producing antibodies. Two widely used expression systems for *E. coli* are lacZ fusions using the pUR series of vectors and trpE fusions using the pATH vectors. The peptides can then be purified, coupled to a carrier protein if desired, and mixed with Freund's adjuvant (to help stimulate the antigenic response of the animal) and injected into rabbits or other appropriate laboratory animals.

Following booster injections at weekly intervals, the rabbits or other laboratory animals are bled and their serum isolated. The serum can be used directly or the polyclonal antibodies purified prior to use by various methods including affinity chromatography.

As will be understood by those skilled in the art, monoclonal antibodies may also be produced using the peptides of the invention. A selected peptide, coupled to a carrier protein if desired, is injected in Freund's adjuvant into mice. After being injected three times over a three week period, the mice spleens are removed and resuspended in phosphate buffered saline (PBS). The spleen cells serve as a source of lymphocytes, some of which are producing antibody of the appropriate specificity. These are then fused with a permanently growing myeloma partner cell, and the products of the fusion are plated into a number of tissue culture wells in the presence of a selective agent such as HAT. The wells are then screened by ELISA to identify those containing cells making binding antibody. These are then plated and after a period of growth, these wells are again screened to identify antibody-producing cells. Several cloning procedures are carried out until over 90% of the wells contain single clones which are positive for antibody production. From this procedure a stable line of clones which produce the antibody is established. The monoclonal antibody can then be purified by affinity chromatography using Protein A Sepharose, ion-exchange chromatography, as well as variations and combinations of these techniques. Truncated versions of monoclonal antibodies may also be produced by recombinant techniques in which plasmids are generated which express the desired monoclonal antibody fragment in a suitable host.

Human neutrophils appear to possess receptors for the peptides of the invention (see, for example, FIG. 6) and it is likely that these peptides, or homologues thereof, occur in humans.

Antibodies to SGP-T and SGP-S, or their human homologues, may be used to determine the circulating concentration of these peptides. By knowing the circulating levels of the SGP-T and SGP-S peptides, a diagnostic tool becomes available to predict the susceptibility of the patient to progress from systemic inflammatory response syndrome SIRS) to the development of septic or nonseptic shock. Low circulating levels of these peptides would indicate increased susceptibility to progression from SIRS to shock, whereas high circulating levels would be indicative of reduced susceptibility to the development of shock.

In addition, knowledge of the circulating levels of SGP-T and/or SGP-S in humans may be used to monitor and adjust dosage levels of the peptides in treatment. Furthermore, this information could be used to predict alternative therapeutic approaches in the management of patients, for example treatment with antibiotics, aggressive volume replacement therapy or the administration of vasoactive agents such as dopamine or vasopressin.

In addition, determination of circulating levels of SGP-T may be useful in determining the reactivity state of neutrophils and monocytes in inflammatory conditions such as arthritis or inflammatory bowel disease. Low circulating levels may indicate the need for neutrophil suppression therapy using the peptides of the invention.

EXAMPLES

The examples are described for the purposes of illustration and are not intended to limit the scope of the invention.

Methods of protein and peptide biochemistry and immunology referred to but not explicitly described in this disclosure and examples are reported in the scientific literature and are well known to those skilled in the art.

Example 1

Isolation, Purification and Sequencing of SGP-T and SGP-S

The purification procedures involved homogenization of rat submandibular glands in 0.1N HCL, centrifugation of the extract at 15,000 g for 1 h, sequential molecular weight cut-off filtration of the supernatant with Amicon 30,000, Centricon 10,000 and 3,000 filters followed by 5 steps of reverse phase high performance liquid chromatography (RP-HPLC) using 20 to 50% acetonitrile. At each step of the purification, biologically active fractions were identified by monitoring their ability to reduce LPS-induced hypotension in sialadenectomized rats. The fractions of submandibular gland extracts generated during purification were assayed by measuring endotoxin induced hypotension in sialadenectomized rates. The extracted glands were lyophilized at each step of the purification to remove acid and/or organic solvents. All fractions were dissolved in 0.9% saline (pH 7.0) at a concentration equivalent of 0.2 µg of original submandibular gland/µl, with each rat receiving 1 µl/kg body weight of the extracts.

Two procedures were used to extract anti-shock activities from submandibular glands. Initially, the glands were homogenized in distilled water containing 50,000 units/mil of Aprotinin (Sigma) and 5 mM benzamidine (Sigma) to inhibit serine proteases (protease inhibitor extraction). One g of frozen submandibular gland in 5 ml of extraction medium was blended for 2 min at high speed in a Waring blender, and the mixture was disrupted further with a ground glass homogenizer. The homogenate was centrifuged at 15,000 g for 1 h with a sorval RC5C maintained at 4° C., and the supernatant, designated the crude homogenate was frozen at −70° C. for subsequent purification. This crude homogenate was then fractionated using several molecular weight exclusion filtrations, which consisted of Diaflow Ultrafilters 30,000 and 10,000 (Amicon Div., W.R. Grace & Co., Danvers, Mass.), performed under 70 psi of nitrogen at 20° C., and Centricon 3000 filters (Amicon Div., Beverly, Mass.) which were centrifuged with a Sorval RC5C centrifuge at 4° C. for 4 h at 7,500 g. The supernatant was then eluted through Sep-Pak columns (Waters Chromatographic Div., Millipore Corp., Milford Corp., Milford, Mass.) with 50% acetonitrile, and after drying the eluant was run on preparative RP-HPLC (20% to 50% acetbnitrile). Further HPLC purification was performed using analytical RP-HPLC columns was performed using analytical RP-HPLC (Vydac C18, 5 µm, 4.6 mm×25 cm). The protein eluting from the HPLC columns was detected monitoring absorbance at 214 nM, a wavelength which detects peptide bonds.

With the protease inhibitor extraction procedures the biological activity was not conserved consistently through to the analytical HPLC stage. This instability was probably due to the limited half-life of the kallikrein inhibitors and the rich array of proteases found in salivary glands. Thus, an acid extraction procedure was applied. The submandibular glands were homogenized in 0.1N HCl to destroy all enzymatic activity, and the extract was purified using the procedures described for the protease inhibition extraction. Using this acid extraction procedure biological activity was conserved through all steps of the purification.

The two peptides were sequenced at the Protein/Peptide Synthesis Unit of The University of Calgary and the Alberta Peptide Institute at The University of Alberta, Edmonton, Alberta.

The peptides were then synthesized, using standard solid phase synthesis Sephadex G-10 and HPLC purified and their amino acid compositions confirmed.

Example 2

Effects of SGP-T and SGP-S on Experimental Endotoxemia

The animal model of endotoxic shock used involves intravenous injection of endotoxin (3.5 mg/kg of lipopolysaccharide (LPS) from *Salmonella typhosa*) into pentobarbital-anaesthetized Sprague-Dawley rats, to produce a fall in mean arterial blood pressure within 3 to 5 minutes. The endotoxin was injected slowly over 1 min. via the jugular vein, and mean arterial blood pressure in mm mercury (MABP) was monitored continuously for 60 min, with the average blood pressure being calculated at 15, 30, 45 and 60 min. Studies were performed on unoperated rats and rats with their submandibular glands removed (sialadenectomized).

The results shown in Table 1 are the averages of three different experiments using the protocol defined above. The data shown represent the average decrease in MABP (dec MABP) and the % Decrease in MABP over the 60 minutes following LPS administration. SGP-S (100µg/kg) and SGP-T (100 µg/kg) were administered 90 min. before LPS. The sialadenectomized rats exhibited a more severe hypotensive response to LPS than unoperated rats. The average MABP for the 60 minutes following LPS injection (MABPaft) was significantly less for the sialadenectomized rats (68.03±3.4 mm Hg) than for the unoperated rats (88.03±3.6 mm Hg). Neither SGP-T nor SGP-S, when given prior to the LPS challenge, had appreciable effects on MABP.

In unoperated rats, SGP-T reduced the drop in MABP elicited by LPS, and this effect was independent of time of administration of the peptide. Overall, SGP-T reduced by 60% the decrease and the percent decrease in MABP induced by endotoxin, relative to pre-LPS values. SGP-S, on the other hand, had no effect on the shock induced by endotoxin in unoperated rats.

In sialadenectomized rats, SGP-S (but not SGP-T) significantly reduced the drop in MABP after LPS, the decrease in MABP after LPS relative to MABP bef, and the percent decrease in MABP relative to MAEP bef.

Figure 1:
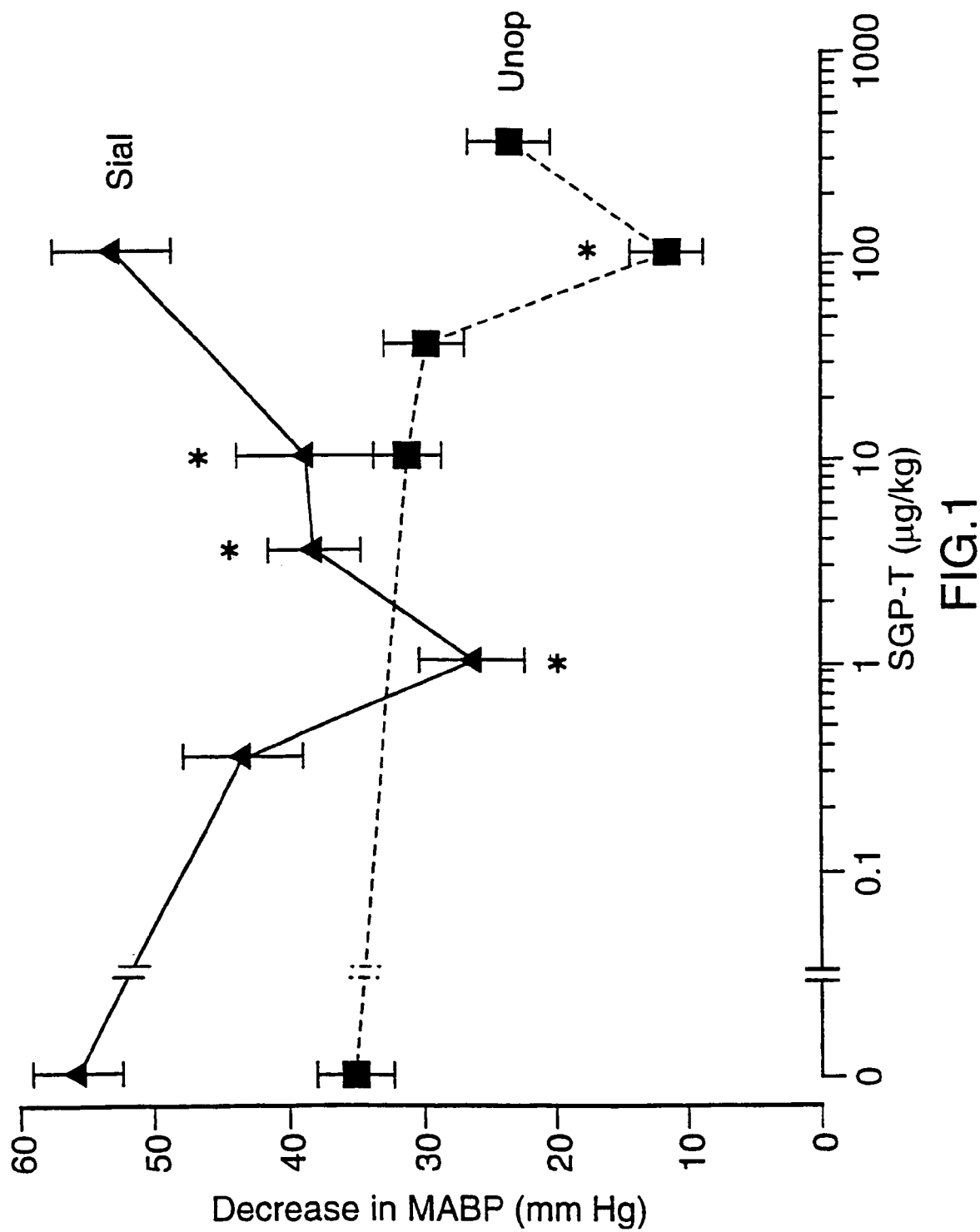
FIG. 1 shows the effect of SGP-T concentration on the average decrease over a 1 hour period in mean arterial blood pressure (MABP) induced by intravenous LPS (*Salmonella typhosa*, 3.5 mg/kg), evaluated in pentobarbital anesthetized unoperated (■) and sialadenectomized (▲) rats. * p<0.05

The dose-response relationship of the inhibitory effect of SGP-T and SGP-S on endotoxin-induced hypotension was also examined and the results are shown in FIG. 1. It can be seen that SGP-T, given intravenously 1.5 hours before LPS, dose-dependently inhibited the decrease in blood pressure induced by the LPS in sialadenectomized rats. SGP-T at doses of 1, 3.5 and 10 µg/kg significantly prevented the LPS-provoked drop in blood pressure. In contrast, saline controls (SGP-T zero) exhibited an average MABP drop of 55 mm Hg. Doses of SGP-T higher than 10 µg/kg were less effective in preventing the shock. The optimal dose of SGP-T for reducing LPS-induced hypotension in unoperated rats was higher than in operated animals.

Example 3

Effect of SGP-T and SGP-S on Anaphylaxis

Cardiovascular Anaphylaxis

Figure 2:
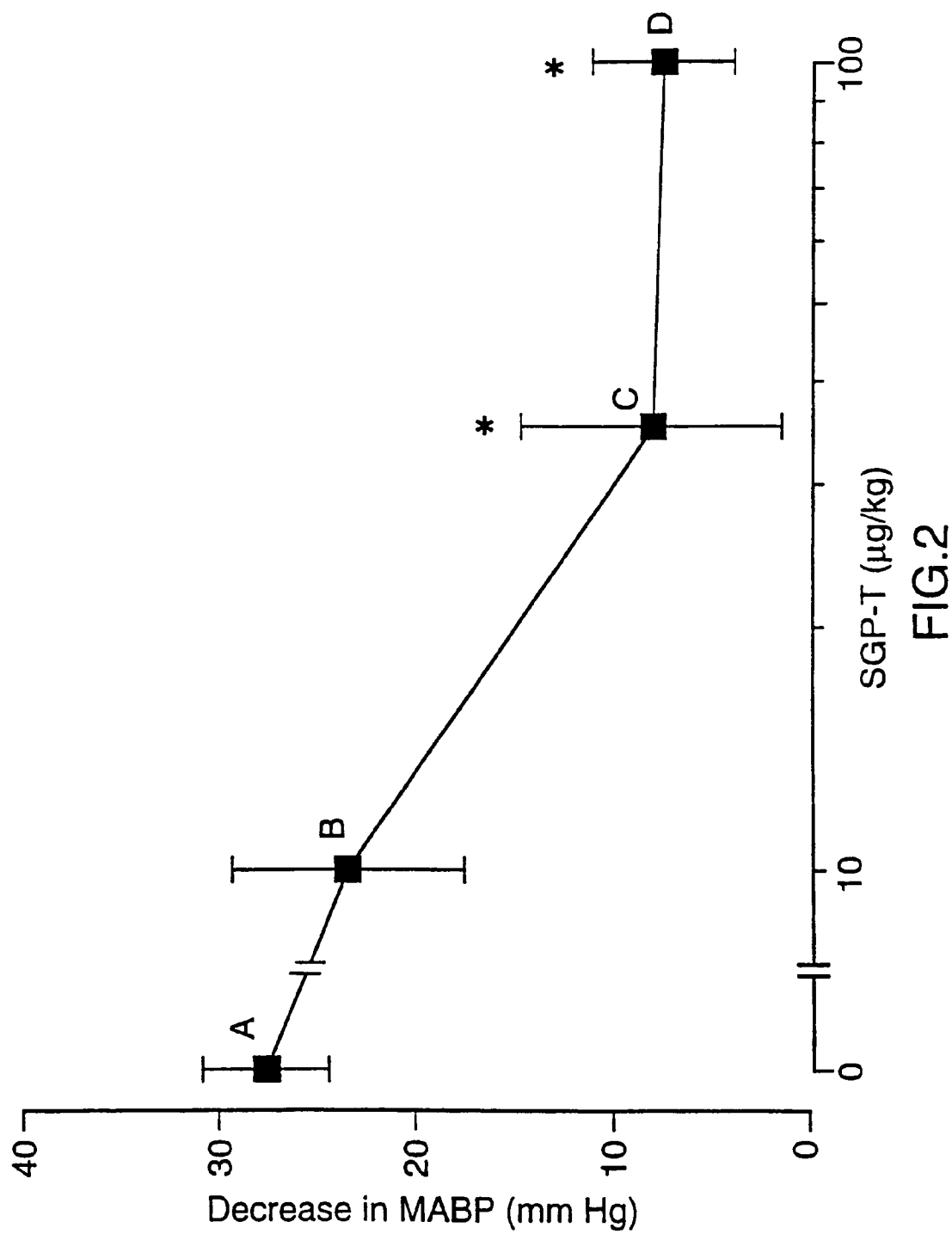
FIG. 2 shows the average decrease in MABP in rats (sensitised 1 month previously with 3000 larvae of the nematode *Nippostrongylus brasiliensis*) challenged by injection of worm antigen (100 worm equivalents), after the following treatments.

The effect of SGP-T on antigen-induced anaphylactic hypotension was examined in Sprague-Dawley rats sensitized 5 weeks previously with the nematode parasite *Nippostrongylys brasiliensis*. Under pentobarbital anesthesia, worm antigen (100 worm equivalents) was injected and arterial blood pressure was followed for 1 hour. The results are'shown in FIG. 2. Whereas rats treated with saline vehicle (SGP-T zero) experienced a drop in blood pressure after antigen challenge of approximately 30 mm Hg, SGP-T given 10 minutes prior to induction of anaphylaxis dose-dependently protected against the anaphylactic hypotension.

Intestinal Anaphylaxis

SGP-T was also effective in preventing intestinal anaphylaxis. FIG. 3 shows that in rats sensitized to the antigen hen egg albumin, instillation of the antigen (EA) into the jejunum after saline pretreatment promoted diarrhoea and disruption of normal fasting gut motility (migrating myoelectric complexes; MMCs). SGP-T, given intravenously at doses as low as 10 µg/kg significantly attenuated these anaphylactic reactions. A dose of 100 µg/kg totally prevented the manifestation of anaphylaxis.

A similar protection against intestinal anaphylaxis was observed in vitro using isolated intestinal (jejunal) segments obtained from egg albumin sensitized rats. SGP-T, at doses as low as 6.8×10⁻⁷M, reduced antigen induced contractions of these isolated intestinal tissues by 60% (data not shown).

Example 4

Modulation of Neutrophil Function by SGP-T

The subcutaneous implantation of a carrageenin-soaked sponge in rats is a model used to evaluate agents that modulate neutrophil chemotaxis, as carrageein is a potent chemotactic agent and the sponge serves as a collecting reservoir.

Under halothane anaesthesia the sponge was removed from its subcutaneous site and the fluid was squeezed from it into a test tube. Following centrifugation at 2,000 g for 10 min, the exudate was decanted and the remaining cells were suspended in 4 ml of 0.9% saline, and their number determined using a Coulter Counter. One ml of the remaining cell suspension was extracted for use in the superoxide assay.

Superoxide Assay

Neutrophils ($10^6$) were suspended in PBS buffer of the following composition: NaCl 137 mM, KCl 2.7 mM, $Na_2HPO_4$, 8.1 mM, $KH_2PO_4$ 1.47 mM, $CaCl_2$ 1.19 mM, $MgCl_2$ 0.54 mM, glucose 7.5 mM and cytochrome C 1.5 mM (Sigma Chemical Co. St. Louis, Mich.) incubated at 37 C. Each sample was read along with a reference sample containing 1440 units of superoxide dismutase (Sigma) in a spectrophotometer (Hitachi, U200 spectrophotometer). The rate of superoxide production in response to $10^{-7}$M phorbol myristate acetate (PMA) or $10^{-5}$ M N-formyl-methionyl-leucyl-phenylalanine (fMLP) was then inferred from the slope. (Derian et al., (1996), Biochemistry 35(4): 1265–9).

Intravenous injections of SGP-T inhibited neutrophil influx into a carrageenin-soaked sponge in a dose-dependent manner (FIG. 4). When the ability of neutrophils obtained from the carrageenin-soaked sponges to generate superoxide anion was evaluated, those obtained from saline-treated rats were totally refractory to f MLP and phorbol myristate acetate (PMA). In contrast, neutrophils collected from rats that received intravenous (via the penile vein) SGP-T 4 hr. before implantation of the sponge were able to generate substantial amounts of superoxide (FIG. 5).

Although the reasons for the lack of a superoxide response in carrageenin exposed neutrophils are unknown, receptor desensitization or uncoupling of the NADPH complex that generates the superoxide are possible explanations. SGP-T abrogates this desensitisation phenomena. By attenuating neutrophil chemotaxis, and by conserving the oxidative capacity of neutrophils, SGP-T provides a new anti-inflammatory agent. Treatment with SGP-T would limit an excessive movement of neutrophils into an inflammatory site, prevent an excessive and intensive generation of superoxide, but still allow the neutrophils to exert oxidative capacity essential for their fight against inflammatory stimuli.

Example 5

Effect of SGP-T on Superoxide Production of Neutrophils

Neutrophils obtained either from carrageenin-soaked sponges implanted subcutaneously in rats, or from the blood of healthy human volunteers, were preincubated with various doses of SGP-T for 30 minutes, then stimulated with $10^{-7}$M PMA and the rate of superoxide anion production determined. At doses less than 1 μM, SGP-T inhibited superoxide anion production by both rat and human neutrophils, although the rat neutrophils were approximately 10-fold less sensitive than human neutrophils to this inhibitor effect (FIG. 6). At higher doses of the peptide(>1 μM), an enhancement of superoxide anion production was evident with human neutrophils.

At 0.001 and 0.01 μM SGP-T, $O_2^-$ production was inhibited by 15 to 20% in human neutrophils, while 10-fold higher concentrations were required for such inhibition with rat neutrophils. Much higher concentrations of SGP-T (10 and 20 μM) stimulated $O_2^-$ production by human neutrophils. Each value is presented as the mean ±SEM, and the number of experiments was between 6 and 12.

Example 6

Structure-Activity Relationships

Analogues and fragments of SGP-T were tested for their ability to inhibit antigen (egg albumin)-induced intestinal contractions, using isolated jejunal segments from egg albumin-sensitised rats, as described in Example 3. Table 2 shows the analogues and fragments tested and the results obtained.

Example 7

Structure-Activity Relationships

Methods

Animals and Tissue Preparation: Male Sprague-Dawley rats were sensitized to egg albumin (ovalbumin, OA) with 50 ng of *Pertussis bordetella* toxin as an adjuvant. Four to six weeks after sensitization, the rats were anaethetised with sodium pentobarbital and the jejunum was removed. Two cm sections of the jejunum were mounted in tissue baths under 0.75 g of isometric tension, and the tissues were allowed to equilibrate for 20 min prior to beginning the experiment.

10 μg of SGP-T or one of its analogues or fragments was added to a bath, while control tissues received the saline vehicle. Following a 10 min incubation, 100 ng of OA prepared in 0.9% saline was added. After the tissue had reached a maximal contractile response, the tissues were washed extensively to remove OA and peptide and, after the tissues had established baseline tension, 20 μg of urecholine (URE; a cholinergic-muscarinic receptor agonist) was added to determine the maximal contractile response of the tissue. The tissues were then removed from the bath, cleared of all underlying mucosa and the weight of the remaining muscle was determined.

Peptides: A series of analogues or fragments of SGP-T was synthesized by conventional methods at the Protein Synthesis Facilities at the University of Calgary and Queen's University.

Data Analysis: The tension (measured in grams) per gram tissue weight generated by each tissue in response to OA and URE was calculated. To normalize for differences in the ability of each tissue segment to contract in response to the muscle stimulants, the contractile response to URE was divided by that obtained upon addition of the sensitizing antigen, OA. Thus, a measure of the antigen-induced contraction was expressed as the URE/OA ratio. An increase in this ratio indicated that the contractile response to OA was decreased by the addition of a test substance.

The data was analyzed using the one-way analysis of variance (ANOVA) and differences between groups was determined using the Student t-test for unpaired samples. The results are shown in FIGS. 7 and 8 and Tables 3 and 4.

Structure Activity Relationships: Ovalbumin-sensitized jejunal tissues responded to the antigen (OA) with a contractile response, and the URE/OA ratio was 4.0±0.4 (Table 3 and FIG. 7; CON). This ratio indicates that URE elicited a contractile response that was 4 times larger than that induced by OA. The URE/OA ratio for SGP-T was 9.4±1.3, indicating that 10 μg of this peptide reduced the anaphylactic reaction by more than 50%.

As examples of possible substitutions, various amino acids of SGP-T were individually replaced by alanine and the effect of these analogues was examined (Table 3 And FIG. 7). Substitution of Aspartic acid (analogue A2) or Isoleucine (I: analogue A3) had a minimal effect on prevention of anaphylaxis. In contrast, the amino terminal Threonine (T; analogue A1), Phenylalanine (F; analogue A4) and to a lesser extent Glutamic acid (E; analogue AS) were important for the prevention of anaphylaxis. Removal of the two carboxy-terminal Glycines (analogue X6) or amidation of the terminal glycine (analogue X7) abolished anti-anaphylactic activity. In contrast, removal of the amino-terminal Threonine, Aspartic and Isoleucine (analogue X8) had no effect on activity.

In view of the activity of the peptide FEGG, analogues of this peptide were examined in the same jejunal assay system (Table 4 and FIG. 8).

In this series of experiments, the URE/OA ratio for control tissues was 5.7±1.0 (FIG. 8 and Table 4). The tripeptide FEG, which contains 2 fewer amino acids than FEGGG, attenuates antigen-induced contraction of the sensitized jejunal segments to the same degree as intact SGP-T. The carboxy-terminal Glycine was replaced with a sarcosine which places a methylene ($CH_3$) group on the alpha carbon of the glycine molecule, without a significant change in biological activity.

Substitution of glycine with a large basic amino acid (Citrulline; Cit), however, or conformationally restricting the carboxy-terminal by substituting a Proline (Pro) for the Glycine, resulted in loss of biological activity.

Example 8

Effects of Analogues of SGP-T on Anaphylactic Hypotension

Methods

Animals and Tissue Preparation: Male Sprague-Dawley rats were sensitized to egg albumin (ovalbumin; OA) with 50 ng of *Pertussin bortella* toxin as an adjuvant. Four to six weeks after sensitization, the rats were anesthetized with sodium pentobarbital. A tracheal tube was inserted and a cannula was inserted into the left ventricle for measuring ventricular peak systolic pressure (VPSP). This cannula was coupled to a blood pressure transducer. A cannula was also inserted into the jugular view for administration of peptide (100 μg/kg) and antigen (100 μg of OA). The peptides were injected intravenously 10 min prior to antigen injection and blood pressure was recorded for 30 min.

In a second study, the peptide feG (D-phenylalanine, D-glutamate, glycine) was administered orally by a stomach tube 1 hour prior to intravenous injection of the sensitizing antigen.

Data Analysis: The percent changes in VSPS induced by anaphyalctic reaction were calculated relative to baseline VPSP. Significance differences within groups were determined with one-way analysis of variance (ANOVA), and between groups with the Student t-test.

The intravenous administration of SGP-T, FEG and feG, at doses of 100 μg/kg, significantly inhibited anaphylactic hypotension, as seen in FIG. 9. feG also significantly reduced anaphylactic hypotension when administered orally, as seen in FIG. 10.

Example 9

Effect of Analocues of SGP-T on Anaphylactic Perturbation of Intestinal Motility Methods Animals and Tissue Preparation: Male Hooded-Listar rats were sensitized to egg albumin (ovalbumin; OA). Two weeks after sensitization, the animals had electrodes implanted into the muscle of the jejunum for recording muscle electrical activity. One week later, the fasted rats received SGP-T or an analogue, either intravenously (injection via penile vein under halothane anaesthesia) or orally (via gastric tube), 20 min before challenge with OA, or bovine serum albumin as control, by intragastric administration.

The disruption of intestinal migrating myoelectric complexes (MMCs) (Scott et al., (1988), J. Physiol., v. 255, pp. G505–511), a measure of intestinal activity, and the presence of diarrhea were used as biological measurements of anaphylaxis. The results are expressed as the percent of the rats exhibiting disrupted MMCs and diarrhea.

Control rats which received an intravenous injection of vehicle (0.9% saline) showed anaphylactic reactions when the sensitizing antigen, OA, was administered intragastrically (FIG. 11). One hundred percent of the rats had disrupted MMC's and 90% exhibited the clinical signal of anaphylaxis, diarrhea. The non-sensitizing antigen, BSA, did not elicit an anaphylactic reaction.

SGP-T, FEG and feG (each administered intravenously at 100 μg/kg) prevented or reduced intestinal anaphylaxis induced by OA. Oral treatment with 350 μg/kg of feG totally abolished all signs of anaphylaxis, as none of the eight animals tested exhibited either diarrhea or disruption of intestinal motility (FIG. 11).

These studies confirm that the tripeptide, FEG, a carboxy terminal fragment of SGP-T, is sufficient to inhibit intestinal anaphyalctic reactions, and that a metabolically stable form of this tripeptide, feG, also possesses anti-anaphylactic activity. These three peptides may be useful in reducing severity of anaphylactic reactions in sensitized individuals.

Example 10

Methods: Sprague-Dawley rats (200–300 g) were sensitized with 1 mg ovalbumin and 50 ng Pertussin toxin (Sigma) (24) one month prior to experimentation. The submandibular glands were removed bilaterally 7 days prior to the experiment by previously described procedures (23). Rats were anesthetized with sodium pentobarbital (65 mg/kg) and a tracheal tube (PE240 polyethylene tubing) was inserted before performing further surgeries. The jugular vein was-cannulated for injection of ovalbumin antigen, which was given as a bolus (100 μg/kg) over 10 sec. The right carotid artery was cannulated and the cannula tip was slowly advanced into the left ventricle, as detected when diastolic pressure fell to near 0 mmHg. The ventricular cannula was connected to a TXD-310 transducer and heart function parameters were recorded using a Digi-Med Heart Performance Analyser (Micro-Med, Louisville, Ky.). The effects of anaphylaxis on heart function were analysed by comparing the changes in ventricular peak systolic pressure (VPSP), and in the rate of ventricular contraction during systole (dP/dt) and relaxation during distole (−dP/dt). Antigen was injected at 10 min. The anaphylactic response was followed for 30 min.

Very rapidly (within 1 min) after the intravenous injection of antigen into ovalbumin-sensitized rats, VPSP dropped and minimal ventricular pressures were measured at 5 min after initiation of the anaphylactic reaction.

In control rats, minimal VPSP decreased by 36.5±7.2% from the pre-antigen values of 165.3±6.3 mm Hg. Over the next 25 min, blood pressure recovered slowly such that, at 30 min after antigen injection, VPSP was only 11.5±4.4% lower than the pre-antigen VPSP values. Submandibular gland peptide, SGP-T, when injected 10 min prior to the antigen, protected the rats against anaphylactic hypotension (FIG. 12). The average decrease in VPSP over the 30 min of the experiment in control rats (saline pretreatment) was 46.2±6.5 mm Hg, whereas in rats that received 10 and 100 µg/kg of SGP-T, the integrated decreases in VPSP were only 16.7±8.3 and 15.9±8.0 mm Hg, respectively. By the end of the experiment, VPSP had attained pre-antigen values in these SGP-T treated rats. Neither lower (10 µg/kg) nor higher doses (350 µg/kg) of SGP-T protected against antigen elicited hypotension. The end diastolic pressure (EDP) was not significantly affected by the anaphylactic response.

To determine if anaphylaxis directly affected heart function, the percent changes in VPSP were plotted against percent changes in dP/dt and −dP/dt. No differences were noted in the slopes of the regression lines of dP/dt or −dP/dt (Table 5) between rats receiving saline and those pretreated with either 35 or 100 µg/kg SGP-T. The regression coefficients were all above 0.9. By analysis of variance, the slopes of the regression lines of dP/dt and −dP/dt were not different from unity.

The rats were anesthetized with intraperitoneal sodium pentobarbital (65 mg/kg), a tracheotomy was performed and the right jugular vein was cannulted (PE50 tubing) for administration of endotoxin. The right carotid artery was cannulated (PE50 tubing) and the cannula tip was slowly advanced into the left ventricle, as detected when diastolic pressure fell to near 0 mmHg. The ventricular cannula was connected to a TXD-310 transducer and heart function parameters were recorded using a Digi-Med Heart Performance Analyzer, Model 200, (Micro-Med, Louisville, Ky.). The data was captured using Digi-med System Integrator, Model 200 (Micro-Med).

Following a 15 to 20 min stabilization period endotoxin (3.5 mg/kg of LPS from Salmonella typhosa; Sigma Chemical Co. St. Louis, Mo.) was injected slowly over 1 min via the jugular vein, and heart function variables were monitored at 1 min intervals for 60 min by sampling the last 10 sec of every minute. The effect of endotoxin on ventricular function variables was evaluated by assessing absolute values of the variables, and their percent changes relative to pre-endotoxin values. The average absolute and percent changes were calculated over the 60 min of the experiment (1–60 min) and at four time intervals (1–15 min, 16–30 min, 31–45 min and 46–60 min) following endotoxin injection. All data are expressed as mean ±SEM. Statistical significance was determined using the Student t-test to identify differences between groups.

The results are shown in FIG. 13. SGP-T reduced significantly the decrease in ventricular peak systolic pressure (VPSP) provoked by antigen (100 µg/kg) administration to ovalbumin-sensitized rats.

A reduction in the severity of decrease in VPSP shows that SGP-T at doses of 35 and 100 µg/kg significantly reduced the drop in blood pressure elicited by the anaphylactic reaction.

Example 11

The effect of the tripeptide FEG on endotoxin-induced hypotension was examined, using the methods described in Example 10. 100 µg/kg FEG was given iv. 30 mins before injection of 3.5 mg/kg LPS (Salmonella typhosa). Examination of the mean arterial blood pressure showed that FEG did not influence endotoxin-induced hypotension, as seen in FIG. 14, which shows MABP at 10 min prior to LPS injection (Before) and 60 min after LPS injection (After).

Example 12

Rats were operated on to remove salivary glands (or controls were sham-operated) one week before challenge with endotoxin. At the time of operation, a temperature sensitive radio transmitter was inserted in the peritoneal cavity. One week after operation, baseline temperatures were recorded by telemetry and SGP-T or saline was injected immediately before intra-peritoneal injection of 150 µg/kg LPS. Temperature was followed for 12 hours. Results are shown in FIG. 15. SGP-T suppressed a late phase (180–420 minutes) of endotoxin-induced fever.

The present invention is not limited to the features of the embodiments described herein, but includes all variations and modifications within the scope of the claims.

REFERENCES

1. Barka T. J Histochem Cytochem 1980; 28: 836–859.
2. Boyer R, Jame F, Arancibia S. Ann Endocrinologie (Paris) 1991; 52: 307–322.
3. Mathison R, Davison J S, Befus A D. Immunology Today 1994; 15: 527–532.
4. Epstein J B, Scully C. J Canadian Dent Ass 1992; 58: 217–221.
5. Kingsnorth A N, Vowles R, Nash J R G. Br J Surg 1990; 77: 409–412.
6. Skinner K, Soper B D, Tepperman B L. Gastroenterology 1981; 81: 335–339.
7. Gray M R, Donnelly R J, Kingsnorth A N. Br J Surg 1991; 78: 1461–1466.
8. Kurachi H, Okamoto S, Oka T. Proc Natl Acad Sci 1985; 82: 5940–5943.
9. Jones Jr D E, Tran-Patterson R, Cui D-M, Davin D, Estell K P, Miller D M. Am J Physiol 1995; 268: G872–G878.
10: Amano O, Matsumoto K, Nakamura T, Iseki S. Growth Factors 1994; 10: 145–151.
11. Tsutsumi O, Kurachi H, Oka T. Science 1986; 233: 975–977.
12. Tsutsumi O, Taketani Y, Oka T. J Endocrinol 1993; 138: 437–443.
13. Rosinski-Chupin et al. (1990), DNA Cell Biol., v. 9; pp. 553–559.
14. Rosinski-Chupin et al. (1988) P.N.A.S. USA, v. 85, pp. 8553–8557.
15. Kemp A, Mellow L, Sabbadini E. Suppression and enhancement of in vitro lymphocyte reactivity by factors in rat submandbular gland extracts. Immunology 1985; 56: 261–267.

16. Abdelhaleem M, Sabbadini E. Identification of immunosuppressive fractions from the rat submandibular salivary gland. Immunology 1992; 76: 331–337.
17. Bissonnette E, Mathison R, Carter L, Davision J S, Befus D: Decentralization of the superior cervical ganglia inhibits mast cell mediated TNFα cytotoxicity 1 Potential role of salivary glands Brain, Behavior & Immunity 1993; 7: 293–300.
18. Carter L, Ferrari, J K, Davision J S, Befus D. Inhibition of neutrophil chemotaxis and activation following decentralization of the superior cervical ganglia. J Leukocyte Biol 1992; 51: 597–602.
19. Saito K, Kato C, Teshigawara H. Saliva inhibits chemiluminescence response, plagocytosis and killing of *Staphylococcus epidermidis* by pplymorphonuclear leukocytes, Infect Immun 1988; 56: 2125–2132.
20. Ramaswamy K, Mathison R, Carter L, Kirk D, Green F, Davison J S & Befus A D. Regulation of inflammatory cell function by bilateral decentralization of the superior cervical ganglion. J Exp Med 1990; 172: 1819–1830.
21. Mathison R, Hogan A, Helmer D, Bauce L, Woolner J, Davison J S, Schultz G, Befus D. Role for the submandibular gland in modulating pulmonary inflammation following induction of systemic anaphylaxis. Brain, Behavior and Immunity 1992; 6: 117–129.
22. Mathison R, Carter L, Mowat C, Befus D, Davison J S. Temporal analysis of the anti-inflammatory effects of decentralization of the superior cervical ganglia Am J Physiol 1994; 266: R1537–R1543.
23. Mathison R, Befus D, Davison J S. Removal of the submandibular glands increases the acute hypotensive response to endotoxin. Circ Shock 1993; 39: 52–58.
24. Kosecka U, Marshall J S, Crow S E, Bienenstock, J & Perdue, M H: Am J. Physiol. 267: G745 (1994).
25. Sambrook et al., (1989), "Molecular Cloning" Cold Spring Harbor, Lab. Press, Cold Spring Harbor, N.Y.
26. Saffran et al., (1979), Can. J. Biochem., v. 57, pp. 548–553.
27. Lundin et al., (1986), Life Sci., v. 38, pp. 703–709.
28. Vilhardt et al., (1986), Gen. Pharmacol., v. 17, pp. 481–483.
29. Amidon et al., (1994), Ann. Rev. Pharmacol. Toxicol., v. 34, pp. 321–341.
30. Choi et al., (1990), Pharm. Res., v. 7, pp. 1099–1106.
31. Remington's Pharmaceutical Sciences, latest edition, Mack Publishing Company (Easton, Pa.).

TABLE 1

| Treatment | MABPbef | MABPaft | decMABP | % Dec |
|---|---|---|---|---|
| Unoperated Rats | | | | |
| Saline (18) | 122.3 ± 3.9 | 88.0 ± 3.6 | −34.2 ± 3.8 | −27.6 ± 2.5 |
| SGP-T (18) | 113.2 ± 3.8 | 99.6 ± 3.8* | −13.6 ± 2.9** | −11.6 ± 2.4** |
| SGP-S (15) | 123.4 ± 3.0 | 95.2 ± 4.3 | −28.1 ± 1.8* | −22.9 ± 1.3 |
| Sialadenectomized Rats | | | | |
| Saline (22) | 125.0 ± 3.8 | 68.0 ± 3.4 | −57.3 ± 4.6 | −44.7 ± 3.1 |
| SGP-T (18) | 123.3 ± 4.9 | 77.2 ± 3.9 | −46.1 ± 4.9 | −36.3 ± 3.3 |
| SGP-S (20) | 119.7 ± 1.8 | 81.6 ± 5.8* | −37.6 ± 4.4* | −32.3 ± 3.9* |

MABPbef = mean arterial blood pressure before LPS;
MABPaft = average MABP for 60 mins after LPS injection;
dec MABP = decrease in MABP after LPS relative to MABPbef;
% Dec = percent decrease in MABP relative to MABPbef.
*different from Saline;
**different from Saline and SGP-S or SGP-T.

TABLE 2

| Identification Number | Peptide | Sequence ID No. | Biological Activity |
|---|---|---|---|
| T2: | STDIFEGG | 10 | − |
| SGP-T: | TDIFEGG | 8 | +++ |
| T3: | ADIFEGG | 2 | − |
| T7: | TAIFEGG | 3 | +++ |
| T10: | TDAFEGG | 4 | + |
| T11: | TDIAEGG | 5 | − |
| T9: | TDIFAGG | 6 | − |
| T5: | TDIFEGG-NH$_2$ | 8 | − |
| T4: | TDIFE | 7 | − |
| T6: | FEGGG | 9 | ++ |
| T8: | FEG | | ++ |

Biological activity = inhibition of antigen-induced jejunal contraction by test peptide.
+++ = highest inhibition (~60%),
++ = moderate inhibition (~40%),
+ = lowest inhibition (~20%),
− = no inhibition.

TABLE 3

| Test Substance | Amino acid Sequence | URE/OA |
|---|---|---|
| Saline | | 4.0 ± 0.4 |
| SGP-T | TDIFEGG | 9.4 ± 1.3* |
| A1 | ADIFEGG | 3.6 ± 0.9 |
| A2 | TAIFEGG | 12.3 ± 2.2* |
| A3 | TDAFEGG | 8.3 ± 1.9* |
| A4 | TDIAEGG | 5.2 ± 1.2 |
| A5 | TDIFAGG | 7.2 ± 1.1* |
| X6 | TDIFE | 1.7 ± 0.3 |
| X7 | TDIFEGG-NH$_2$ | 4.3 ± 0.7 |
| X8 | FEGGG | 10.7 ± 2.0* |
| X9 | STDIFEGG | 3.58 ± 1.07 |

*$P < 0.05$

TABLE 4

| Test Substance | Amino acid Sequence | URE/OA |
|---|---|---|
| Saline | | 5.7 ± 1.0 |
| SGP-T | TDIFEGG | 13.9 ± 5.6 |
| FEG | FEG | 12.1 ± 2.8 |
| Sar | FE-Sarcosine | 10.0 ± 1.6 |
| Cit | FE-Citrulline | 5.0 ± 1.1 |
| Pro | FE-Proline | 6.2 ± 1.3 |

TABLE 5

Linear relationship between % VPSP and % dP/dt and % −dP/dt.

| Treatment | Equation of Regression Lines | dP/dt − dP/dt |
|---|---|---|
| Saline | Y = 1.19(±0.04)X + 0.02(±0.02) | Y = 1.39(±0.05)X + 0.05(±0.03) |
| 35 µg/kg SGP-T | Y = 1.17(±0.09)X − 0.01(±0.01) | Y = 1.62(±0.09)X + 0.19(±0.03) |
| 10 µg/kg SGP-T | Y = 1.00(±0.05)X + 0.02(±0.02) | Y = 1.55(±0.04)X + 0.01(±0.02) |

We claim:

1. A method for treating an inflammatory reaction in a mammal comprising administering to the mammal a peptide of the formula: $X^1$—$R^1$—$X^2$—$R^2$ wherein $X^1$ is an aromatic amino acid residue;

$X^2$ is any amino acid residue; and $R^1$ is $NH_2$— or an amino acid sequence $X^3$—$X^4$—$X^5$ wherein $X^3$ is an aliphatic amino acid residue having a side chain hydroxyl group and $X^4$ and $X^5$ are the same or different and are any amino acid residue and wherein $R^2$ is a sequence of 1 to 3 amino acid residues which are the same or different and are aliphatic amino acid residues, or a fragment or derivative of said peptide of the formula $R^1$—$X^1$—$X^2$—$R^2$ effective to treat an inflammatory reaction.

2. The method of claim 1 wherein $X^1$ is phenylalanine;

$R^1$ is $NH_2$—; and $R^2$ is an aliphatic amino acid residue.

3. The method of claim 1 wherein $X^1$ is phenylalanine;

$X^2$ is Glu or Ala;

$R^2$ is selected from the group consisting of Gly, Gly-Gly and Gly-Gly-Gly; and $R^1$ is $NH_2$— or $X^3$—$X^4$—$X^5$ wherein $X^3$ is Thr, $X^4$ is Asp or Ala and $X^5$ is Ile or Ala.

4. The method of claim 1 wherein
$X^1$ is phenylalanine;
$X^2$ is Glu;
$R^1$ is $NH_2$—; and
$R^2$ is selected from the group consisting of Gly, Gly-Gly and Gly-Gly-Gly.

5. The method of claim 1 wherein the peptide is selected from the group consisting of:
    (a) Thr-Asp-Ile-Phe-Glu-Gly-Gly (Sequence ID NO:8);
    (b) Thr-Ala-Ile-Phe-Glu-Gly-Gly (Sequence ID NO:3);
    (c) Thr-Asp-Ala-Phe-Glu-Gly-Gly (Sequence ID NO:4);
    (d) Thr-Asp-Ile-Phe-Ala-Gly-Gly (Sequence ID NO:6);
    (e) Phe-Glu-Gly-Gly-Gly (Sequence ID NO:9);
    (f) Phe-Glu-Gly-Gly (Sequence ID NO:11);
    (g) Phe-Ala-Gly-Gly-Gly (Sequence ID NO: 12); and
    (h) Phe-Glu-Sarcosine.

6. The method of claim 1 wherein $R^2$ is a sequence of 1 to 3 amino acid residues which are the same or different and are selected from the group consisting of glycine, sarcosine, azetidine, nipecotic acid and pipecotic acid.

7. The method of claim 1 wherein at least one amino acid of said peptide is a D amino acid.

8. The method of claim 1 wherein the peptide is Phe-Glu-Gly.

9. The method of claim 1 wherein the peptide is DPhe-DGlu-Gly.

10. The method of claim 1 wherein the inflammatory reaction is associated with a disorder selected from the group consisting of a rheumatic disorder, inflammatory bowel disease, post-ischemic inflammation and systemic inflammatory response syndrome.

11. A method for reducing the infiltration of neutrophils into an inflammatory site in a mammal comprising administering to the mammal a peptide of the formula: $X^1$—$R^1$—$X^2$—$R^2$
    wherein $X^1$ is an aromatic amino acid;
    $X^2$ is any amino acid residue; and
    $R^1$ is $NH_2$— or an amino acid sequence $X^3$—$X^4$—$X_5$
    wherein $X^3$ is an aliphatic amino acid residue having a side chain hydroxyl group and $X^4$ and $X^5$ are the same or different and are any amino acid residue and wherein $R^2$ is a sequence of 1 to 3 amino acid residues which are the same or different and are aliphatic amino acid residues, or a fragment or derivative of said peptide of the formula $X^1$—$R^1$—$X^2$—$R^2$ effective for reducing the infiltration of neutrophils into an inflammatory site.

12. The method of claim 11 wherein
$X^1$ is phenylalanine;
$R^1$ is $NH_2$—; and
$R^2$ is an aliphatic amino acid residue.

13. The method of claim 11 wherein
$X^1$ is phenylalanine;
$X^2$ is Glu or Ala
$R^2$ is selected from the group consisting of Gly, Gly-Gly and Gly-Gly-Gly; and
$R^1$ is $NH_2$— or $X^3$—$X^4$—$X^5$ wherein $X^3$ is Thr, $X^4$ is Asp or Ala and $X^5$ is Ile or Ala.

14. The method of claim 11 wherein
$X^1$ is phenylalanine;
$X^2$ is Glu;
$R^1$ is $NH_2$—; and
$R^2$ is selected from the group consisting of Gly, Gly-Gly and Gly-Gly-Gly.

15. The method of claim 11 wherein the peptide is selected from the group consisting of:
    (a) Thr-Asp-Ile-Phe-Glu-Gly-Gly (Sequence ID NO:8);
    (b) Thr-Ala-Ile-Phe-Glu-Gly-Gly (Sequence ID NO:3);
    (c) Thr-Asp-Ala-Phe-Glu-Gly-Gly (Sequence ID NO:4);
    (d) Thr-Asp-Ile-Phe-Ala-Gly-Gly (Sequence ID NO:6);
    (e) Phe-Glu-Gly-Gly-Gly (Sequence ID NO:9);
    (f) Phe-Glu-Gly-Gly (Sequence ID NO:11);
    (g) Phe-Ala-Gly-Gly-Gly (Sequence ID NO: 12); and
    (h) Phe-Glu-Sarcosine.

16. The method of claim 11 wherein $R^2$ is a sequence of 1 to 3 amino acid residues which are the same or different and are selected from the group consisting of glycine, sarcosine, azetidine, nipecotic acid and pipecotic acid.

17. The method of claim 11 wherein at least one amino acid of said peptide is a D amino acid.

18. The method of claim 11 wherein the peptide is Phe-Glu-Gly.

19. The method of claim 11 wherein the peptide is DPhe-DGlu-Gly.

20. A method for inhibiting activation of neutrophils in a mammal comprising administering to the mammal a peptide of the formula:
    $R^1$—$X^1$—$X^2$—$R^2$
    wherein $X^1$ is an aromatic amino acid;
    $X^2$ is any amino acid residue; and
    $R^1$ is $NH_2$— or an amino acid sequence $X^3$—$X^4$—$X^5$
    wherein $X^3$ is an aliphatic amino acid residue having a side chain hydroxyl group and $X^4$ and $X^5$ are the same or different and are any amino acid residue and wherein $R^2$ is a sequence of 1 to 3 amino acid residues which are the same or different and are aliphatic amino acid residues, or a fragment or derivative of said peptide of the formula $X^1$—$R^1$—$X^2$—$R^2$ effective for inhibiting activation of neutrophils.

21. The method of claim 20
wherein $X^1$ is phenylalanine;
$X^2$ is Glu;
$R^1$ is $NH_2$—; and
$R^2$ is selected from the group consisting of Gly, Gly-Gly and Gly-Gly-Gly.

22. The method of claim 20 wherein the peptide is Phe-Glu-Gly or DPhe-DGlu-Gly.

23. The method of claim 20 wherein the peptide is Phe-Glu-Gly-Gly-Gly.

24. The method of claim 1 wherein the peptide is Phe-Glu-Gly-Gly-Gly.

25. The method of claim 11 wherein the peptide is Phe-Glu-Gly-Gly-Gly.

26. The method of claim 1 wherein
$X^2$ is an acidic amino acid residue;
$R^1$ is $NH_2$—; and
$R^2$ is a sequence of 1 to 3 amino acid residues which are the same or different and are aliphatic amino acid residues.

27. The method of claim 11 wherein
$X^2$ is an acidic amino acid residue;
$R^1$ is $NH_2$—; and
$R^2$ is a sequence of 1 to 3 amino acid residues which are the same or different and are aliphatic amino acid residues.

28. The method of claim 20 wherein
$X^2$ is an acidic amino acid residue;
$R^1$ is $NH_2$—; and
$R^2$ is a sequence of 1 to 3 amino acid residues which are the same or different and are aliphatic amino acid residues.

* * * * *

SEQUENCE LISTING

<160> NUMBER OF SEQ ID NOS: 12

<210> SEQ ID NO 1
<211> LENGTH: 6
<212> TYPE: PRT
<213> ORGANISM: Salmonella typhosa

<400> SEQUENCE: 1

Ser Gly Glu Gly Val Arg
 1               5

<210> SEQ ID NO 2
<211> LENGTH: 7
<212> TYPE: PRT
<213> ORGANISM: Salmonella typhosa

<400> SEQUENCE: 2

Ala Asp Ile Phe Glu Gly Gly
 1               5

<210> SEQ ID NO 3
<211> LENGTH: 7
<212> TYPE: PRT
<213> ORGANISM: Salmonella typhosa

<400> SEQUENCE: 3

Thr Ala Ile Phe Glu Gly Gly
 1               5

<210> SEQ ID NO 4
<211> LENGTH: 7
<212> TYPE: PRT
<213> ORGANISM: Salmonella typhosa

<400> SEQUENCE: 4

Thr Asp Ala Phe Glu Gly Gly
 1               5

<210> SEQ ID NO 5
<211> LENGTH: 7
<212> TYPE: PRT
<213> ORGANISM: Salmonella typhosa

<400> SEQUENCE: 5

Thr Asp Ile Ala Glu Gly Gly
 1               5

<210> SEQ ID NO 6
<211> LENGTH: 7
<212> TYPE: PRT
<213> ORGANISM: Salmonella typhosa

<400> SEQUENCE: 6

Thr Asp Ile Phe Ala Gly Gly
 1               5

<210> SEQ ID NO 7
<211> LENGTH: 5
<212> TYPE: PRT
<213> ORGANISM: Salmonella typhosa

```
<400> SEQUENCE: 7

Thr Asp Ile Phe Glu
 1               5

<210> SEQ ID NO 8
<211> LENGTH: 7
<212> TYPE: PRT
<213> ORGANISM: Salmonella typhosa

<400> SEQUENCE: 8

Thr Asp Ile Phe Glu Gly Gly
 1               5

<210> SEQ ID NO 9
<211> LENGTH: 5
<212> TYPE: PRT
<213> ORGANISM: Salmonella typhosa

<400> SEQUENCE: 9

Phe Glu Gly Gly Gly
 1               5

<210> SEQ ID NO 10
<211> LENGTH: 8
<212> TYPE: PRT
<213> ORGANISM: Salmonella typhosa

<400> SEQUENCE: 10

Ser Thr Asp Ile Phe Glu Gly Gly
 1               5

<210> SEQ ID NO 11
<211> LENGTH: 4
<212> TYPE: PRT
<213> ORGANISM: Salmonella typhosa

<400> SEQUENCE: 11

Phe Glu Gly Gly
 1

<210> SEQ ID NO 12
<211> LENGTH: 5
<212> TYPE: PRT
<213> ORGANISM: Salmonella typhosa

<400> SEQUENCE: 12

Phe Ala Gly Gly Gly
 1               5
```